(12) United States Patent
Light et al.

(10) Patent No.: US 6,396,262 B2
(45) Date of Patent: *May 28, 2002

(54) METHOD AND APPARATUS FOR SHORT TERM INSPECTION OR LONG TERM STRUCTURAL HEALTH MONITORING

(75) Inventors: Glenn M. Light; Hegeon Kwun; Sang-Young Kim; Robert L. Spinks, Jr., all of San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/855,460

(22) Filed: May 15, 2001

Related U.S. Application Data

(63) Continuation-in-part of application No. 09/815,219, filed on Mar. 22, 2001, which is a continuation-in-part of application No. 09/519,530, filed on Feb. 25, 2000, now Pat. No. 6,294,912.
(60) Provisional application No. 60/124,763, filed on Mar. 17, 1999.

(51) Int. Cl.[7] .......................... G01N 27/82; G01N 29/04; G01N 9/24; G01R 33/12
(52) U.S. Cl. .......................... 324/240; 324/220; 73/643
(58) Field of Search .................................. 324/240, 219, 324/220, 221, 228, 238, 239; 73/578, 579, 598, 629, 643

(56) References Cited

U.S. PATENT DOCUMENTS 6,294,912 B1 * 9/2001 Kwun ........................ 324/240

* cited by examiner

*Primary Examiner*—Walter E. Snow
(74) *Attorney, Agent, or Firm*—Gunn, Lee & Hanor, P.C.

(57) ABSTRACT

A method and apparatus is shown for implementing magnetostrictive sensor techniques for the nondestructive short term inspection or long term monitoring of a structure. A plurality of magnetostrictive sensors are arranged in parallel on the structure and includes (a) a thin ferromagnetic strip that has residual magnetization, (b) that is coupled to the structure with a couplant, and (c) a coil located adjacent the thin ferromagnetic strip. By a transmitting coil, guided waves are generated in a transmitting strip and coupled to the structure and propagate along the length of the structure. For detection, the reflected guided waves in the structure are coupled to a receiving strip and are detected by a receiving magnetostrictive coil. Reflected guided waves may represent defects in the structure.

19 Claims, 19 Drawing Sheets

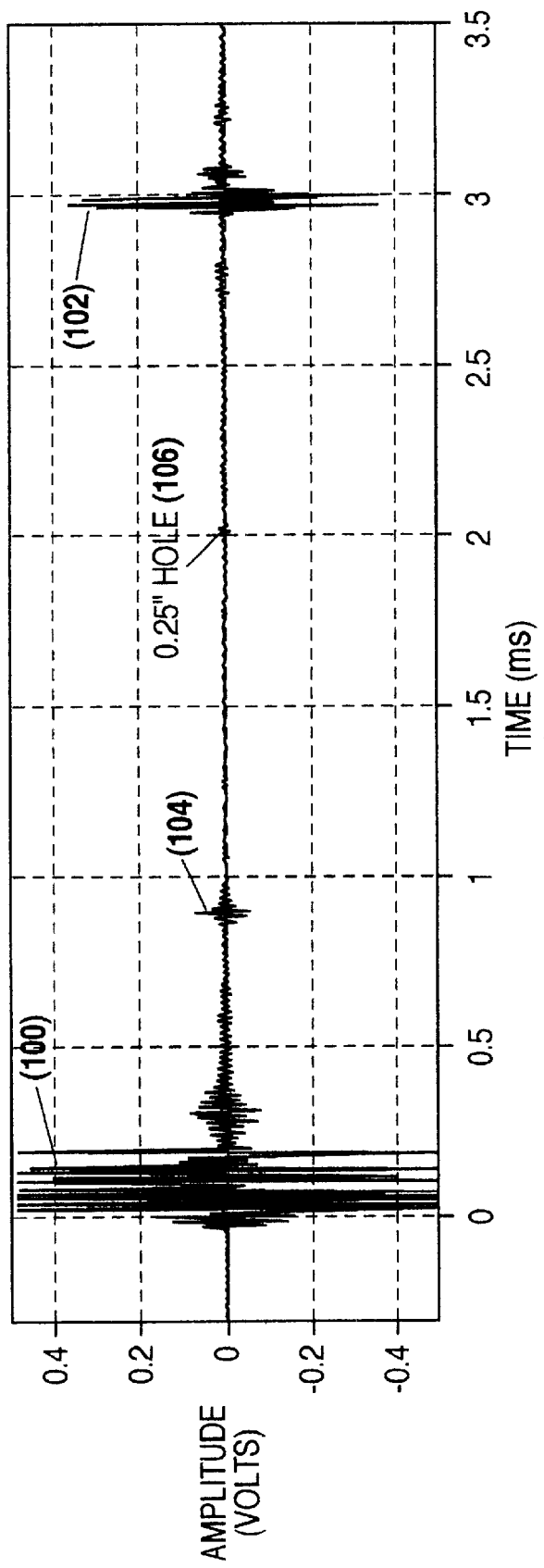

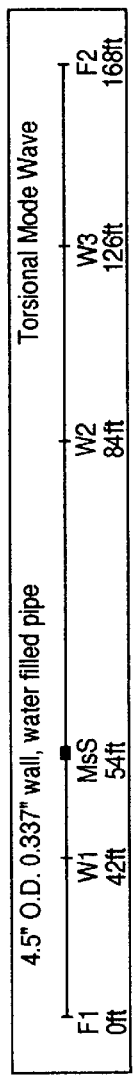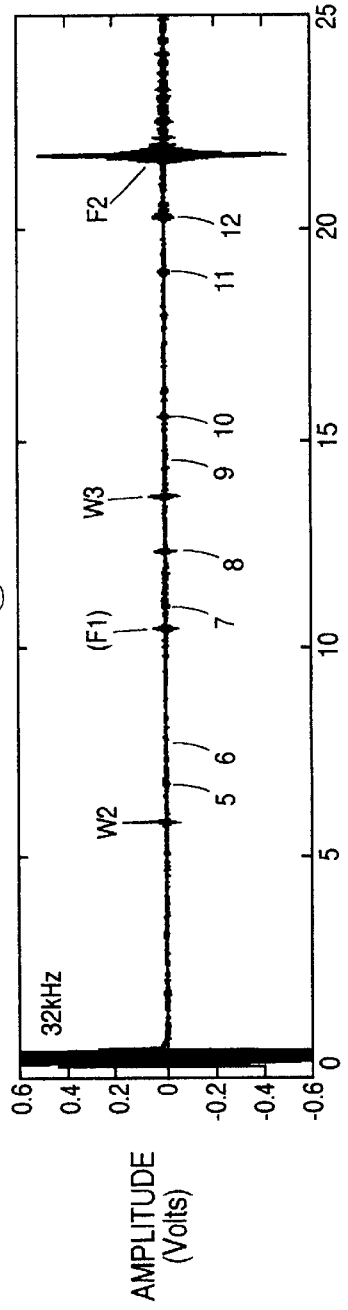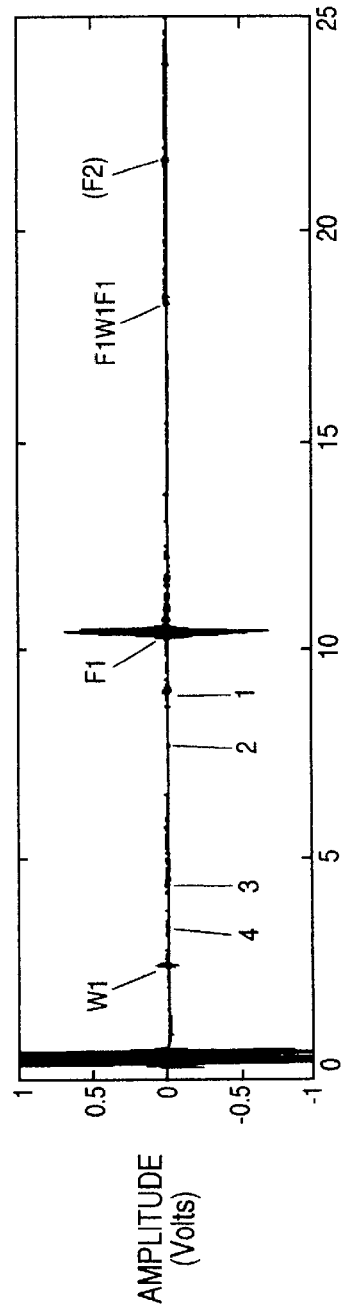
Fig. 12A
Fig. 12B
Fig. 12C

METHOD AND APPARATUS FOR SHORT TERM INSPECTION OR LONG TERM STRUCTURAL HEALTH MONITORING

This is a continuation-in-part patent application depending from U.S. patent application Ser. No. 09/815,219, filed Mar. 22, 2001, which is a continuation-in-part patent application depending from U.S. patent application Ser. No. 09/519,530, filed Feb. 25, 2000, now U.S. Pat. No. 6,294,912, which depends on provisional Patent Application Ser. No. 60/124,763, filed on Mar. 17, 1999.

BACKGROUND OF THE INVENTION

1. Field of the Invention

The present invention relates generally to methods and devices for short term inspection of structures, or long term monitoring of the health of a structure. The present invention relates more specifically to a magnetostrictive sensor based system for short term inspection or long term monitoring of the health of a structure.

2. Description of the Related Art

Magnetostrictive effect refers to the phenomena of a physical dimension change in ferromagnetic materials that occurs through variations in magnetization. In magnetostrictive applications, the generation and detection of mechanical waves is typically achieved by introducing a pulse current into a transmitting coil adjacent to a ferromagnetic material. The change in magnetization within the material located near the transmitting coil causes the material to change its length locally in a direction parallel to the applied field. This abrupt local dimension change, which is the magnetostrictive effect, generates a mechanical wave (called guided wave) that travels through the ferromagnetic material with a certain fixed speed (which is usually less than the speed of sound). When the mechanical wave is reflected back from the end of the ferromagnetic material, or from a defect in the ferromagnetic material, and reaches a detection coil, the mechanical wave generates a changing magnetic flux in the detection coil as a result of the inversed magnetostrictive effect. This changing magnetic flux induces an electric voltage within the detection coil that is proportional to the magnitude of the mechanical wave. The transmitting coil and the detection coil can be identical.

Advantages of using the magnetostrictive effect in non-destructive evaluation (NDE) applications include (a) the sensitivity of the magnetostrictive sensors, (b) durability of the magnetostrictive sensors, (c) no need to couple the sensor to the material being investigated, (d) long range of the mechanical waves in the material under investigation, (e) ease of implementation, and (f) low cost of implementation.

The use of magnetostrictive sensors (MsS) in the nondestructive evaluation (NDE) of materials has proven to be very effective in characterizing defects, inclusions, and corrosion within various types of ferromagnetic and non-ferromagnetic structures. A MsS launches a short duration (or a pulse) of guided waves in the structure under investigation and detects guided wave signals reflected from anomalies such as defects in the structure. Since guided waves can propagate long distances (typically 100 feet or more), the MsS technique can inspect a global area of a structure very quickly. In comparison, other conventional NDE techniques such as ultrasonics and eddy current inspect only the local area immediately adjacent to the probes used. Therefore, the use of magnetostrictive sensors offers a very cost effective means for inspecting large areas of steel structures such as strands, cables, pipes, and tubes quickly with minimum support requirements such as surface preparation, scaffolding, and insulation removal. The ability to use magnetostrictive sensors with little preparation of the object under inspection derives from the fact that direct physical contact between the sensors and the material is not required.

Efforts have been made in the past to utilize magnetostrictive sensor technologies in association with the inspection of both ferromagnetic and non-ferromagnetic materials. Included in these efforts are systems described in U.S. Pat. Nos. 5,456,113; 5,457,994; and 5,501,037, which are each commonly owned by the assignee of the present invention. The disclosures of U.S. Pat. Nos. 5,456,113; 5,457,994; and 5,501,037, provide background on the magnetostrictive effect and its use in NDE and are therefore incorporated herein by reference. These efforts in the past have focused primarily on the inspection of pipe, tubing and steel strands/cables wherein the geometry of the structure is such that the cross-sectional diameter is small in comparison to the length of the structure. While these systems and their application to longitudinal structures find significant applications, there are yet other structures that could benefit from the use of magnetostrictive based NDE.

Other efforts have been made in the past to utilize sensors that measure magnetic flux and/or acoustic waves in structural materials. These efforts have included those described in the following patents:

U.S. Pat. No. 3,555,887 issued to Wood on Jan. 19, 1971 entitled Apparatus for Electroacoustically Inspecting Tubular Members for Anomalies Using the Magnetostrictive Effect and for Measuring Wall Thickness. This patent describes a system designed to direct a mechanical wave through the thickness dimension of a long tubular member. The sensitivity of the device is limited to the directing of a wavefront normal to the surface of the material under inspection and immediately back to a sensor when reflected from an opposite wall or an anomaly.

U.S. Pat. No. 4,881,031 issued to Pfisterer, et al. on Nov. 14, 1989 entitled Eddy Current Method and Apparatus for Determining Structure Defects in a Metal Object Without Removing Surface Films or Coatings. This patent describes a method for establishing localized eddy currents within ferromagnetic materials and recognizes the presence and effect of a coating in order to identify and quantify corrosion beneath the coating. As with other eddy current methods, the ability to inspect a material is limited to the area immediately adjacent to the sensor.

U.S. Pat. No. 5,544,207 issued to Ara, et al. on Aug. 6, 1996 entitled Apparatus for Measuring the Thickness of the Overlay Clad in a Pressure Vessel of a Nuclear Reactor. This patent describes a system directed solely to the measurement of magnetic field variations that result from the distribution of the magnetic field through overlays of varying thickness. The system utilizes a magnetic yoke that is placed in close contact with the surface of the overlay clad of the pressure vessel.

U.S. Pat. No. 5,687,204 issued to Ara, et al. on Nov. 11, 1997 entitled Method of and Apparatus for Checking the Degradation of a Pressure Vessel of a Nuclear Reactor. This patent describes a system similar to the earlier issued Ara, et al. patent and utilizes a magnetic yoke having an excitation coil and a magnetic flux measuring coil that are placed in close contact with the inner wall of the pressure vessel. The hysteresis magnetization characteristics formed by the magnetic yoke and the pressure vessel wall are measured. Degradation of the material comprising the pressure vessel is inferred from a determination of the hardness of the material which is determined from the coercive forces obtained by analyzing the hysteresis characteristics of the magnetization.

In general, a magnetostrictive sensor consists of a conductive coil and a means for providing a DC bias magnetic field in the structure under inspection. The means for providing a bias magnetic field can include the use of either permanent magnets or electromagnets. In a transmitting magnetostrictive sensor, an AC electric current pulse is applied to the coil. The resulting AC magnetic field (a changing magnetic field) produces guided waves in an adjacent ferromagnetic material through the magnetostrictive effect. For pipes, cables, tubes, and the like, the waves are typically launched along the length of the longitudinal structure. In the receiving magnetostrictive sensor, a responsive electric voltage signal is produced in the conductive coil when the guided waves (transmitted or reflected from anomalies within the material) pass the sensor location, through the inverse magnetostrictive effect.

With MsS techniques, defects are typically detected by using the pulse-echo method well known in the field of ultrasonics. Since the sensor relies on the magnetostrictive behavior found in ferrogmagnetic materials, this technology is primarily applicable to the inspection of ferromagnetic components such as carbon steel piping or steel strands. It is also applicable, however, to the inspection of nonferrous components if a thin layer of ferromagnetic material, such as nickel, is plated or coupled onto the component in the area adjacent to the magnetostrictive sensors.

The magnetostrictive sensor technique has the advantage of being able to inspect a large area of material from a single sensor location. Such sensors have, for example, been used to accurately inspect a length of pipe or cable of significantly more than 100 feet. Further, magnetostrictive sensor techniques are comprehensive in their inspection in that the methods can detect both internal and external defects, thereby providing a 100% volumetric inspection. The techniques are also quite sensitive, being capable of detecting a defect with a cross-section less than 1% of the total metallic cross-section of cylindrical structures such as pipes, tubes, or rods. Finally, as indicated above, magnetostrictive sensor techniques do not require direct physical contact between the component surface and the sensor itself. This eliminates the need for surface preparation or the use of a couplant.

Application to Plate Type and Containment Structures

In recent years, there have been many reported occurrences of steel containment liners degrading at commercial nuclear power plants. Due to the aging of such facilities and the increased requirements for inspection, incidents of degradation are likely to increase. The structural degradation of these liners, especially corrosion damage, is an important concern since the liners are designed to provide a leak-tight pressure boundary for the nuclear containment. Many other industrial uses of plate type ferromagnetic materials could benefit from more frequent inspections to determine the state of deterioration, the location of faults, and the likelihood of failure. In most instances in the past, inspections of large plate type objects (such as large aboveground storage tanks) have required either very expensive off-line inspections or statistical samplings of randomly selected local areas that are for the most part less than reliable. It has heretofore been difficult to carry out a thorough inspection of a plate type structure, or a structure comprised of a plurality of plate type sheets of material, without high cost and long down time for the object under inspection. It would be desirable to use the magnetostrictive sensor technique for detecting and locating various anomaly characteristics within plate type materials. Such techniques could be used for detecting and locating wall thickness reductions in liners, such as those described above, that might be caused by corrosion over time. If such a system were applicable, it would be possible to inspect otherwise inaccessible regions of containment liners and the like that are either imbedded in concrete or adjacent to flooring or equipment that cannot be moved.

It would therefore be desirable to implement magnetostrictive sensor techniques in conjunction with plate type structures in a manner similar to, and with the accuracy of, such systems utilized in conjunction with cylindrical structures. It would be desirable if an inspection of plate type and cylindrical structures could be carried out in an efficient manner that did not require full access to the surface of the plate or the inner or outer surface of cylindrical structures such as pipes and tubes. Such a magnetostrictive sensor system would be able to investigate large volumes of a plate type or cylindrical structure, including pipes and tubes, and would provide a cost effective global inspection of the structure.

SUMMARY OF THE PRESENT INVENTION

It is therefore an object of the present invention to provide a sensor device for implementing magnetostrictive based NDE in association with pipes and tubes in order to evaluate the condition of the structures and to determine the presence of anomalies indicative of fractures, deteriorations, and the like.

It is a further object of the present invention to provide a magnetostrictive sensor appropriate for use in conjunction with the inspection of pipes and tubes that is capable of transmitting and receiving guided waves within the pipes and tubes and generating signals representative of the characteristics of such waves appropriate for the analysis and detection of anomalies therein.

It is a further object of the present invention to provide magnetostrictive sensor devices appropriate for use in conjunction with the inspection of pipes and tubes that inspect the entire structure for anomalies, corrosion, fractures, and the like in a cost effective manner.

It is a further object of the present invention to provide a method for the inspection of pipes and tubes that includes the use of a magnetostrictive sensor specifically adapted for directing guided waves along the length of the pipe or tube and detecting such waves as may be reflected from anomalies along the pipe or tube.

It is yet another object of the present invention to provide a method and apparatus for nondestructive evaluation of pipes and tubes utilizing magnetostrictive sensors that generate and detect shear horizontal waves along the length of the item being inspected.

It is yet another object of the present invention to provide a magnetostrictive sensor that is suitable for low frequency operation (200 kHz or less), has good sensitivity and long inspection range, and is relatively tolerate to liftoff.

It is still another object of the present invention to provide a method and apparatus for nondestructive evaluation of pipes using magnetostrictive sensors that propagate guided waves in a circumferential direction around the pipe.

Another object of the present invention is to provide a method and apparatus for nondestructive evaluation of pipes and tubes using magnetostrictive sensors with torsional waves that has better defect detectability particularly in liquid filled pipes or tubes.

Still another object of the present invention is to provide a method and apparatus for the nondestructive evaluation of pipes and tubes that requires no permanent DC bias magnets or electromagnets and, thus is easier to apply.

Another object of the present invention is to provide a method and apparatus for the nondestructive evaluation of pipes and tubes that has a reduced setup time and therefore a lower inspection cost.

In fulfillment of these and other objectives, the present invention provides a method and apparatus for implementing magnetostrictive sensor techniques for the nondestructive evaluation of plate type structures such as walls, vessels, enclosures, and the like. The system includes magnetostrictive sensors specifically designed for application in conjunction with welded plate type structures that generate guided waves in the plates which travel through the plate in a direction parallel to the surface of the plate. Similarly structured sensors are positioned to detect the guided waves (both incident and reflected) and generate signals representative of the characteristics of the guided waves detected. The system anticipates the use of either discrete magnetostrictive transmitters and receivers or the use of a single magnetostrictive sensor that operates to both transmit and detect the guided waves. The sensor structure is longitudinal in nature and generates a guided wave having a wavefront parallel to the longitudinal direction of the sensor. Appropriate electronics associated with the process of generating the guided waves and controlling the propagation direction of the generated wave through the magnetostrictive transmitter as well as detecting, filtering, and amplifying the guided waves at the magnetostrictive receiver, are implemented as is well known in the art. Signal analysis techniques, also known in the art, are utilized to identify anomalies within the plate type structure. The method utilizes pattern recognition techniques as well as comparisons between signal signatures gathered over time from the installation of the structure under investigation to a later point after deterioration and degradation may have occurred.

The magnetostrictive sensors can also be used to detect defects in cylindrical structures such as to detect defects in electric resistance welding, such as in pipes that are welded along a seam thereof. For example, a magnetostrictive transmitter can be placed on one side of the pipe being investigated and a magnetostrictive receiver on the other side of the pipe. By propagating a guided wave in circumferential direction around the pipe, any defects in the pipe can immediately be detected, such as in the area of the weld.

For generation and detection of the symmetrical (S) or the anti-symmetrical (A) Lamb wave mode in a plate type structure, the DC magnet or field required for MsS operation is applied parallel to the direction of wave propagation. For generation and detection of the shear horizontal (SH) wave mode, the DC magnetic field required for MsS operation is applied perpendicular to the direction of wave propagation. Due to the enclosed nature of cylindrical structures such as pipes and tubes, the shear horizontal wave can be induced to act as a torsional wave along the length of the pipe or tube. The generation of a shear horizontal or torsional wave along the length of the pipe or tube allows defect detectability that will not be hampered by the presence of liquid in the pipe or tube.

Current flow along the longitudinal axis of a pipe or tube will cause magnetization of a ferromagnetic pipe or tube in the circumferential direction. This magnetization can be used for the transmission and detection of torsional waves that flow along the pipe and tube and any reflections thereof. The reflections may be from anomalies or defects in the pipe or tube.

Also, a thin ferromagnetic strip that is magnetized in the circumferential direction may be wrapped around and held tightly against the pipe or tube. Thereafter, a torsional wave may be generated or detected where the ferromagnetic strips are located along the pipe or tube. The circumferential magnetization around the pipe or tube is in the ferromagnetic strip. It is very important to hold the ferromagnetic strip in tight surface contact with the pipe or tube so that the full effect of the torsional wave can be felt and detected in either the transmitter or receiver coils adjacent thereto.

In another embodiment of the present invention, a thin strip of a ferromagnetic material that can retain residual magnetization, such as nickel, is prepared an appropriate width and length. The width of the strip depends upon the operating frequency of the magnetostrictive device. The length of the strip depends upon the structure to be monitored. For example, for a pipe, the length is slightly shorter than the circumference of the pipe. For a plate-type structure, the length is typically 10 inches or less.

Residual magnetization is induced along the length of the strip by applying an external magnetic field to the strip along its length and then removing the external magnetic field. Afterwards, the strip is coupled to the structure to be monitored with an appropriate material, such as epoxy. For a pipe, the strip is bonded around the circumference of the pipe. For a plate-type structure, the strip is bonded normal to the direction of wave propagation to be used for inspection. For short term inspection, a viscous couplant, such as honey, may be used to couple the strip on a temporary basis to the structure being inspected.

After coupling the strip to the structure to be inspected, a coil is either wrapped around or placed adjacent to the magnetized strip. A minimum of two strips and coils are used, one for transmitting and one for receiving the magnetostrictive signals.

For long term monitoring, the transmitters and receivers are encased or covered in a manner to protect them from the environment. Wires from the magnetostrictive transmitters and receivers are easily accessible whereby the transmitters and sensors can be electrically monitored by appropriate magnetostrictive instrumentation.

For short term inspection, the signal obtained indicates if there is a defect in the structure being inspected. For long term monitoring, a baseline signal is obtained and stored in the computer. Thereafter, additional signals are obtained periodically from the magnetostrictive transmitters and receivers with changes in the signal indicating changes in the structure being inspected.

The guided wave normally used in the method just described for piping applications is a torsional wave and in plate-type structures is a shear horizontal wave.

BRIEF DESCRIPTION OF THE DRAWINGS

FIG. 12 are plots of torsional wave signals received through the system of the present invention depicted in FIG. 11 when used to test a pipe filled with water, utilizing a 32 kHz torsional wave mode in a 4.5 inch outside diameter steel pipe having a 0.337 inch thick wall and 168 foot length.

DETAILED DESCRIPTION OF THE PREFERRED EMBODIMENT

Figure 1:
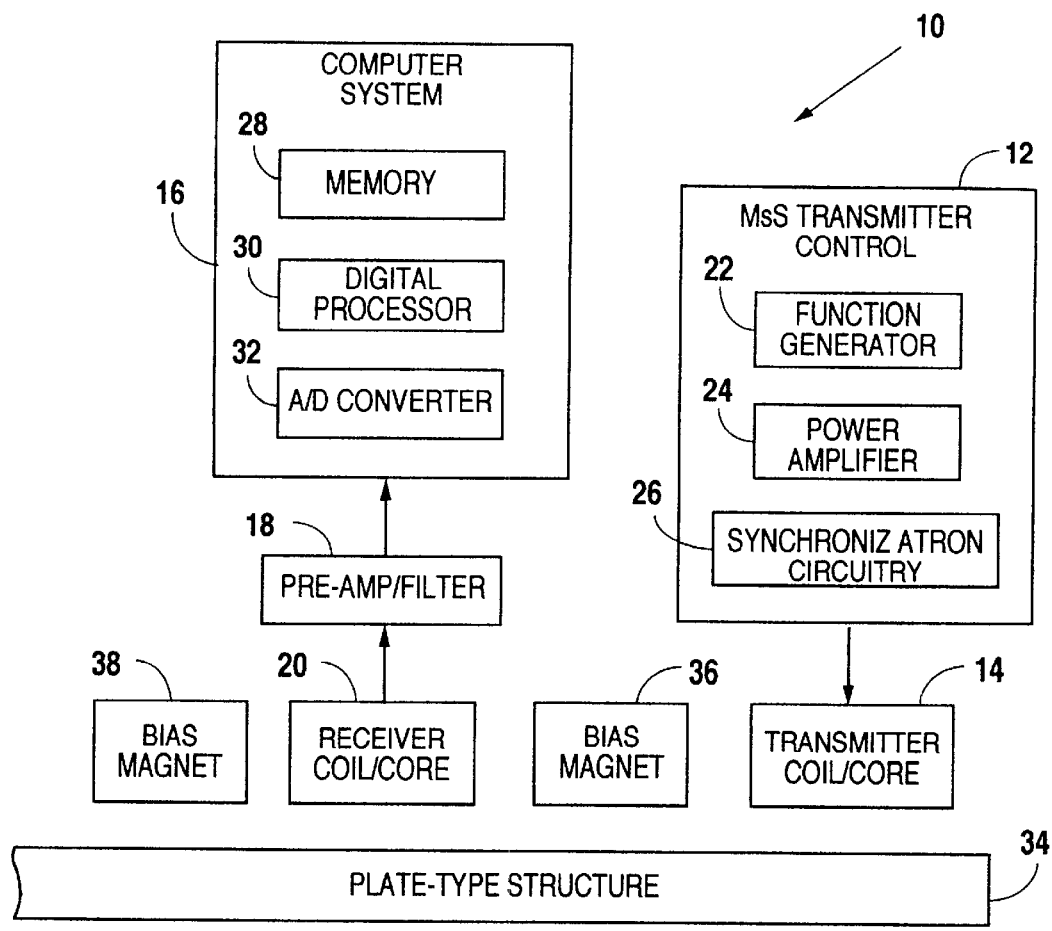
FIG. 1 is a schematic block diagram showing the components of the system of the present invention.

As indicated above, the present invention utilizes the basic methodological approach of earlier developed magnetostrictive sensor techniques associated with the inspection of cylindrical structures such as pipe, tubes, and the like. The basic system of such techniques is combined with a novel magnetostrictive sensor for application to plate type structures. Reference is made first to FIG. 1 for a general description of the complete system utilized to carry on the inspection of a plate type structure. Inspection system 10 includes a magnetostrictive sensor transmitter control 12 and an associated transmitter coil/core 14. Transmitter coil/core 14 is positioned adjacent to the surface of plate type structure 34. Also positioned near the surface of plate type structure 34 is receiver coil/core 20. Receiver coil/core 20 is positioned to detect reflected waves within plate type structure 34 and to thereby generate a signal representative of the wave characteristics that are reflected from a defect present in the structure. Receiver coil/core 20 is connected to preamp/filter 18 which in turn is connected to computer system 16.

Magnetostrictive sensor transmitter control 12 is comprised of function generator 22, power amplifier 24, and synchronization circuitry 26. These elements together generate an appropriate signal for driving transmitter coil/core 14 and thereby generate guided waves within plate type structure 34.

Computer system 16 is comprised of memory 28, digital processor 30, and analog to digital converter 32. These components together receive, digitize, and analyze the signal received from receiver coil/core 20. The signal contains wave characteristics indicative of the characteristics of the reflected guided waves present in plate type structure 34.

Both transmitter coil/core 14 and receiver coil/core 20 have associated with them bias magnets 36 and 38, respectively. Bias magnets 36 and 38 are positioned adjacent the coils/cores 14 and 20 near plate type structure 34 in order to establish a bias magnetic field to facilitate both the generation of guided waves within structure 34 and the appropriate detection of reflected guided waves.

Figure 2:
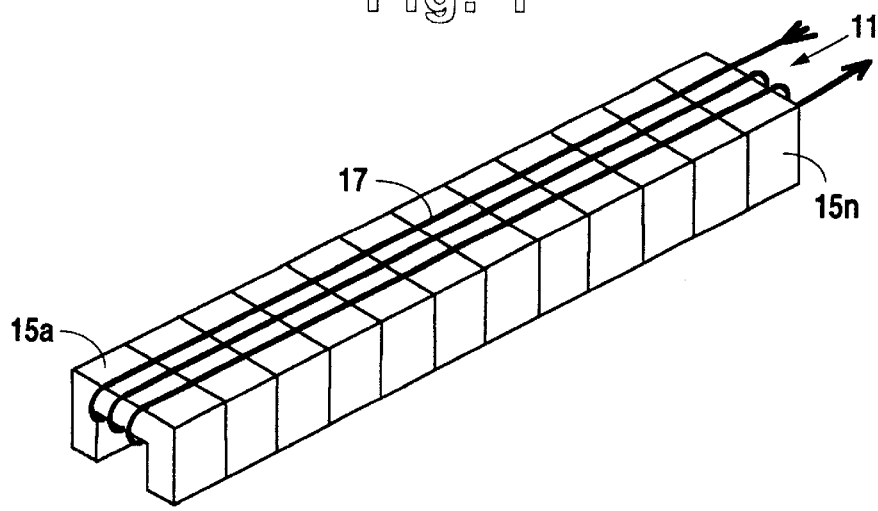
FIG. 2 is a perspective view of a magnetostrictive sensor of the present invention.

Reference is now made to FIG. 2 for a detailed description of the novel magnetostrictive sensor structure utilized in the present invention. Magnetostrictive sensor 11 as shown in FIG. 2 could be utilized as either transmitter coil/core 14 or receiver coil/core 20 described above in FIG. 1. Magnetostrictive sensor 11 is comprised of a plurality of U-shaped cross-sectional cores stacked in a lengthwise direction to form a sensor with a longitudinal axis that is long in comparison to its cross-section. Core elements 15a through 15n in the preferred embodiment may be made from a stack of U-shaped ferrites, transformer steel sheets, mild steel, or permanent magnets. The core elements 18a through 15n could have other shapes; however, U-shaped or E-shaped core elements have been found to be more efficient. If an E-shaped core is used, a transmitter may be located on one part of the E with a receiver on the other part of the E.

Surrounding the stack of U-shaped cores 15*a* through 15*n* is wire coil 17. The number of turns for coil 17 is dependent upon the driving current and the magnetic permeability of core 15 and may be varied as is well known in the art.

Figure 3:
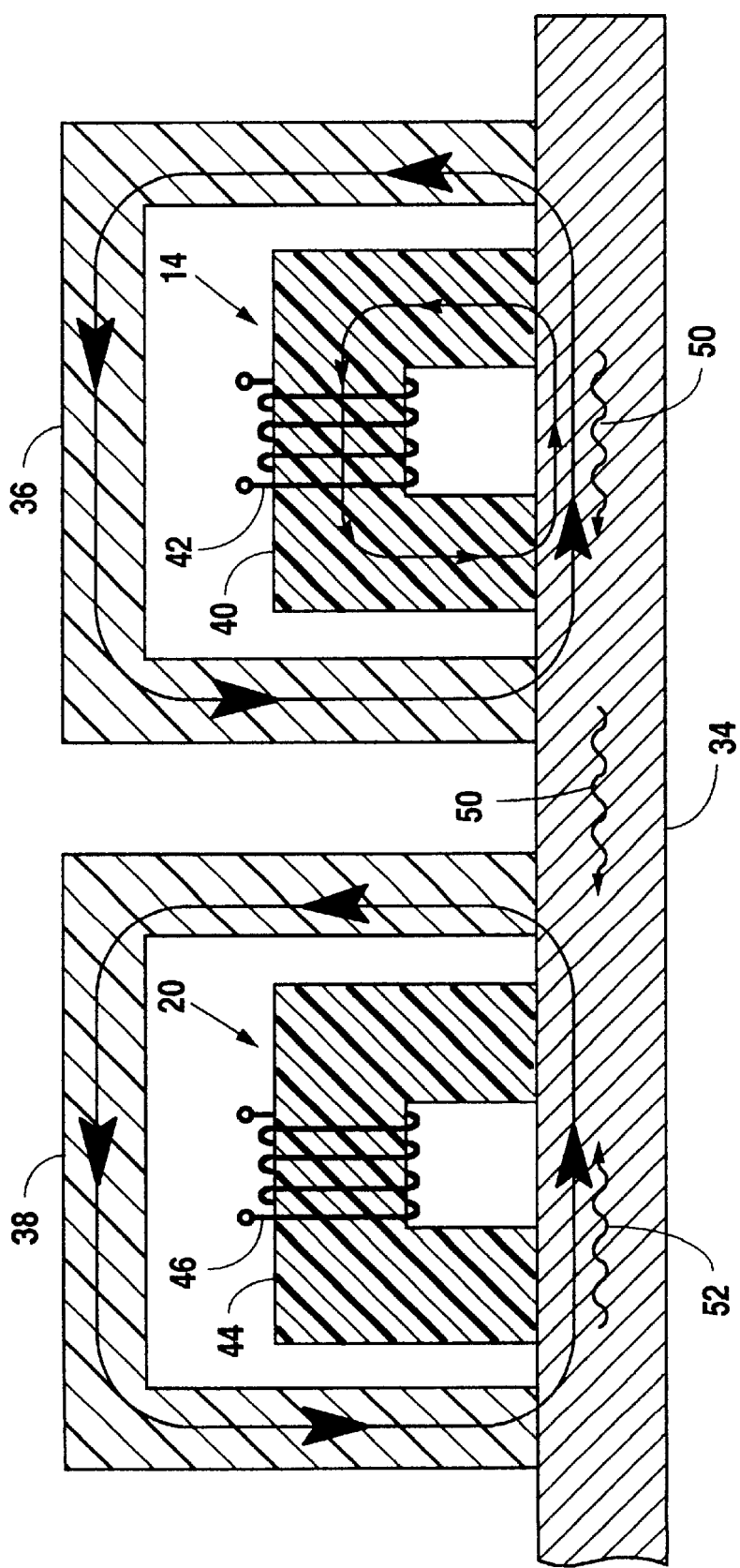
FIG. 3 is a cross-sectional view of the implementation of the sensors of the present invention in conjunction with a plate type structure.

FIG. 3 shows in cross-sectional view the application of a pair of sensors structured as shown in FIG. 2 and implemented in conjunction with the methods of the present invention. In FIG. 3, a cross-section of plate type structure 34 is shown with transmitter coil/core 14 and receiver coil/core 20 positioned on the plate. The view in FIG. 3 of both transmitter coil/core 14 and receiver coil/core 20 is cross-sectional in nature in order to show the establishment of a magnetic flux within plate type structure 34. Associated with each of the coils/cores 14 and 20 are bias magnets 36 and 38. In FIG. 3, bias magnets 36 and 38 are shown placed over coils/cores 14 and 20. It is understood that in the actual implementation of the present invention, bias magnets 36 and 38 may be one or two magnets. What is necessary is that a magnetic field be generated in plate type structure 34 under the transmitter coil/core 14 and the receiver coil/core 20. It is only critical that the DC bias magnetic fields established by bias magnets 36 and 38 are established within the volume of plate type structure 34 under transmitter coil/core 14 and under receiver coil/core 20 as appropriate.

Transmitter coil/core 14 is comprised of core material 40 and coil windings 42. Together these components, as driven by the magnetostrictive sensor transmitter control (not shown), operate to generate changes in the magnetic field established by bias magnet 36 within plate type structure 34. This time-varying or AC magnetic field within plate type structure 34 generates a guided wave that propagates in a direction parallel to the surface of plate type structure 34. This guided wave is depicted as wave 50 in FIG. 3 and propagates in a direction away from transmitter coil/core 14. If, as shown in FIG. 3, transmitter coil/core 14 is placed on the surface of plate type structure 34, with the longitudinal axis of coil/core 14 directed into the drawing page in the view shown, wave 50 would propagate in two directions away from the longitudinal axis of coil/core 14 and through plate type structure 34. This would serve to investigate the volume of plate type structure 34 bounded by the length (long axis) of the magnetostrictive sensor utilized. In this manner, an inspection "sweep" of a volume of plate type structure 34 can be carried out generally equal in width to the length of the magnetostrictive sensor.

The arrangement of the magnetostrictive sensor utilized as the detection coil in the present invention is essentially the same as the arrangement for the transmitter coil. In FIG. 3, receiver coil/core 20 is comprised of core material 44, shown in cross-section, as well as coil windings 46. Bias magnet 38 is likewise positioned over receiver coil/core 20. This arrangement establishes a bias magnetic field within plate type structure 34 that fluctuates according to the presence of reflected guided waves within the material adjacent the sensor. In FIG. 3, reflected guided waves are depicted as 52 proximate to receiver coil/core 20 and are detected thereby. In this manner, guided waves passing through plate type structure 34 under receiver coil/core 20 are detected and "translated" into voltage fluctuations in coil 46 in a manner that generates an appropriate signal for analysis by the balance of the electronics of the system of the present invention (not shown).

As indicated above, the methods and apparatus of the present invention can be utilized in conjunction with discrete magnetostrictive transmitters and receivers or in conjunction with a single magnetostrictive sensor operable as both a transmitter and a receiver. In the latter case, the structures described in FIG. 3 would be limited to a single magnetostrictive sensor of the configuration shown for either transmitter coil/core 14 or receiver coil/core 20.

In another alternative approach, one with greater practical application, two transmitter sensors and two receiver sensors may be used when the sensors are controlled by appropriate phasing. In this manner, the direction of the interrogating beam may be controlled. As an example, when the transmitter generates the wave in a first position (+) direction, the return signals may be detected by a receiver controlled to detect waves traveling in the negative (−) direction. As mentioned above, this control is achieved by phasing the two sensors appropriately, a process well known in the field of NDE techniques. In this manner, an inspection of the plate may be carried out first to one side of the transmitting sensor and then by simply switching the sensor instrumentation an inspection may be carried out to the opposite side of the transmitting sensor. Various other inspection techniques known and used with magnetostrictive sensors may likewise apply with the methods and structures of the present invention.

Figure 4:
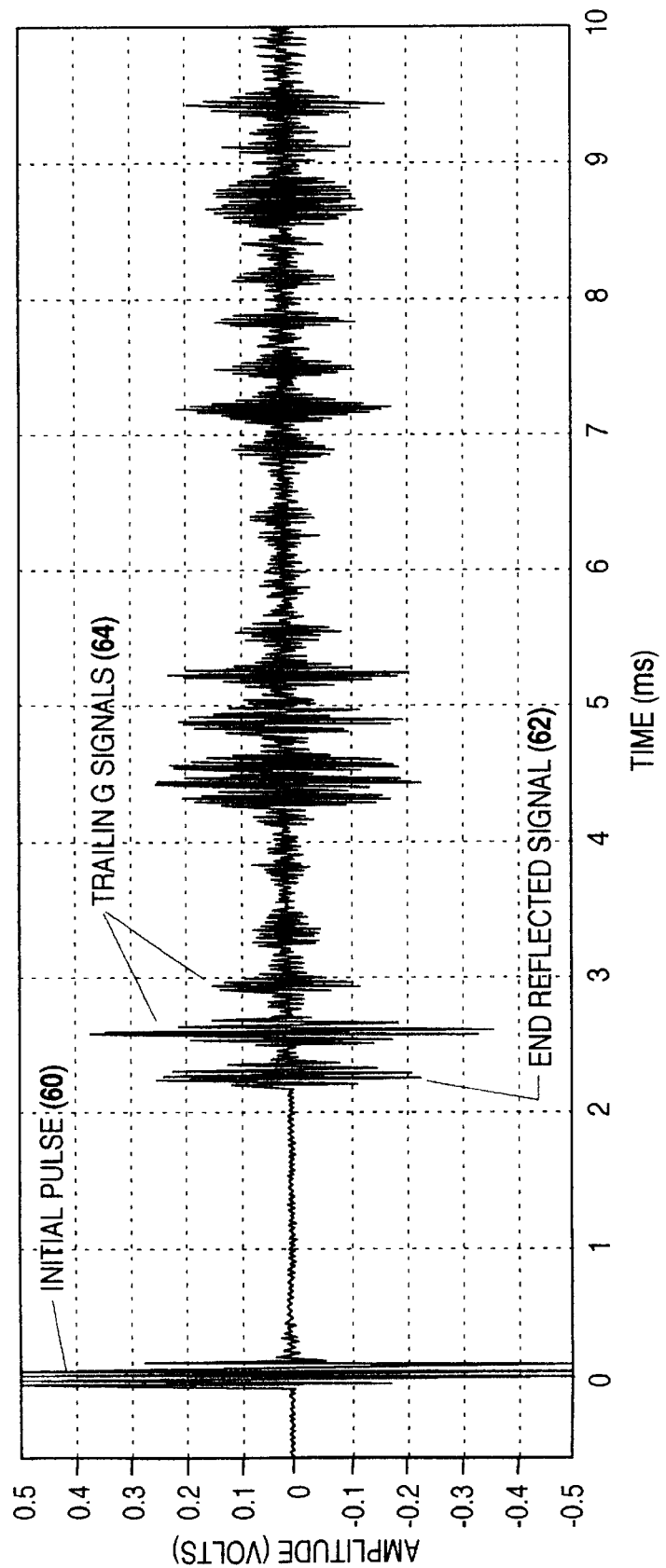
FIG. 4 is a plot of a signal received through the system of the present invention utilizing a 60 kHz symmetric ($S_0$) wave mode signal in a 4 foot wide, 20 foot long, 0.25 inch thick steel plate.
Figure 5:
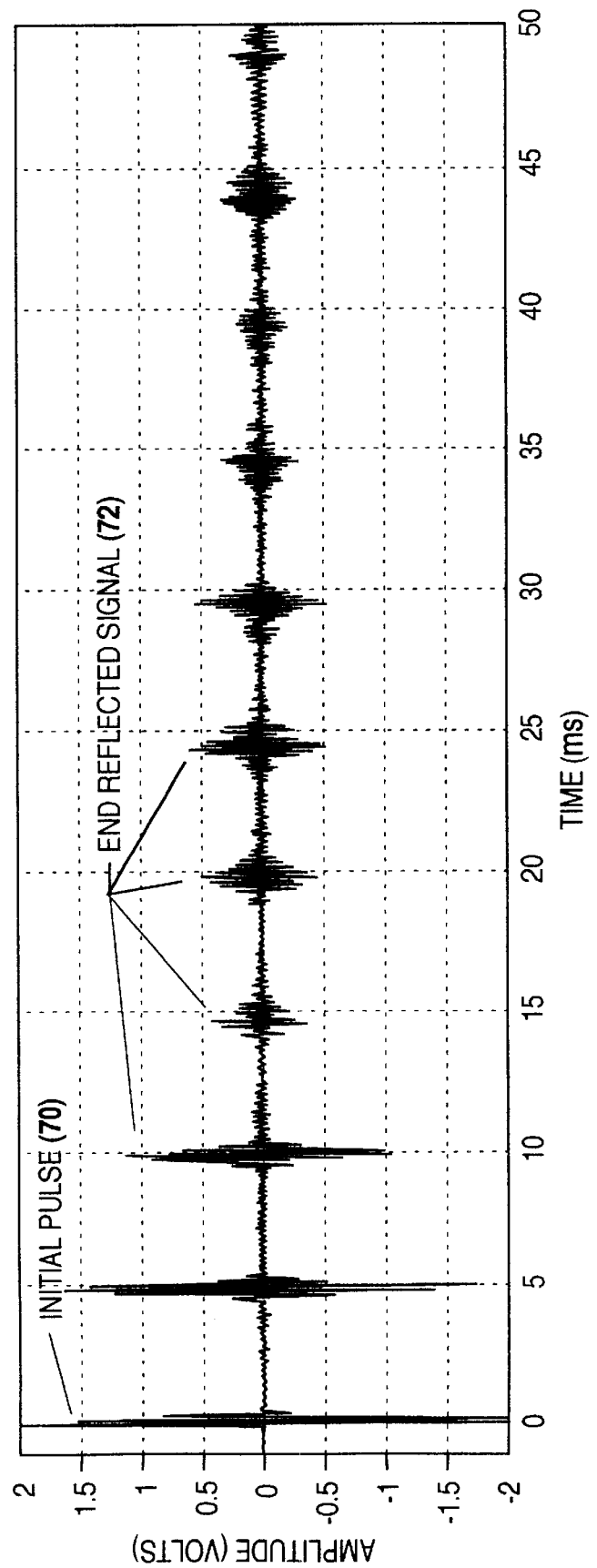
FIG. 5 is a plot of a signal received through the system of the present invention in conjunction with the structure associated with FIG. 4 for a 40 kHz anti-symmetric ($A_0$) wave mode signal.

Reference is now made to FIGS. 4 and 5 for a detailed description of sample data acquired from a 0.25 inch thick, 20 foot long, and 4 foot wide steel plate investigated by the devices and methods of the present invention.

The signal represented in FIG. 4 shows the first symmetric wave mode ($S_0$) in the plate while the signal depicted in FIG. 5 shows the first anti-symmetric wave mode ($A_0$). FIG. 4 is a time varying amplitude plot of a 60 kHz magnetostrictive sensor signal taken from the above described steel plate geometry. The wave is directed through appropriate orientation of the sensor and propagates in the long direction within the steel plate. The signal components identified in FIG. 4 include the initial pulse 60, end reflected signal 62, and trailing signals 64. Likewise in FIG. 5, initial pulse 70 is indicated, as are end reflected signals 72.

Anomalies within the path of the guided wave generated within the material would, as is known in the art, generate signal components having amplitudes sufficient for identification within either of the two signals shown in FIGS. 4 and 5. In this manner, characteristics of anomalies detected within the plate type structure can be identified and located in the direction of wave propagation away from the magnetostrictive sensor. As is known in the art, the relative location of an anomaly may be identified by the position of the signal characteristic indicative of the anomaly in time relationship with the initial pulse (indicative of the position of the sensor) and the end reflected signals 62 and 72.

Figure 6:
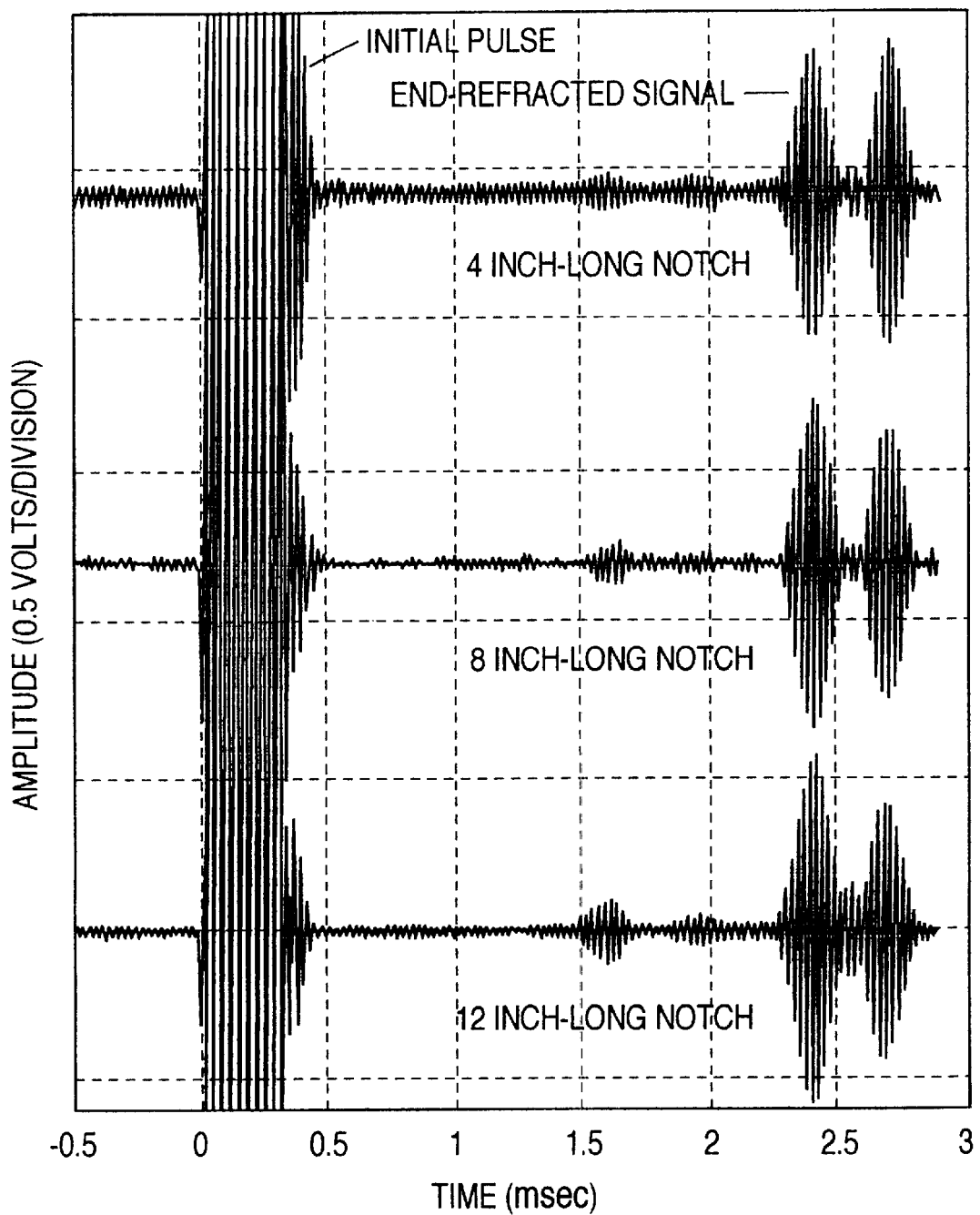
FIG. 6 is a plot of three signals received through the system of the present invention utilizing a 40 kHz symmetric ($S_0$) wave mode signal in a 4 foot wide, 20 foot long, 0.25 inch thick steel plate.
Figure 7:
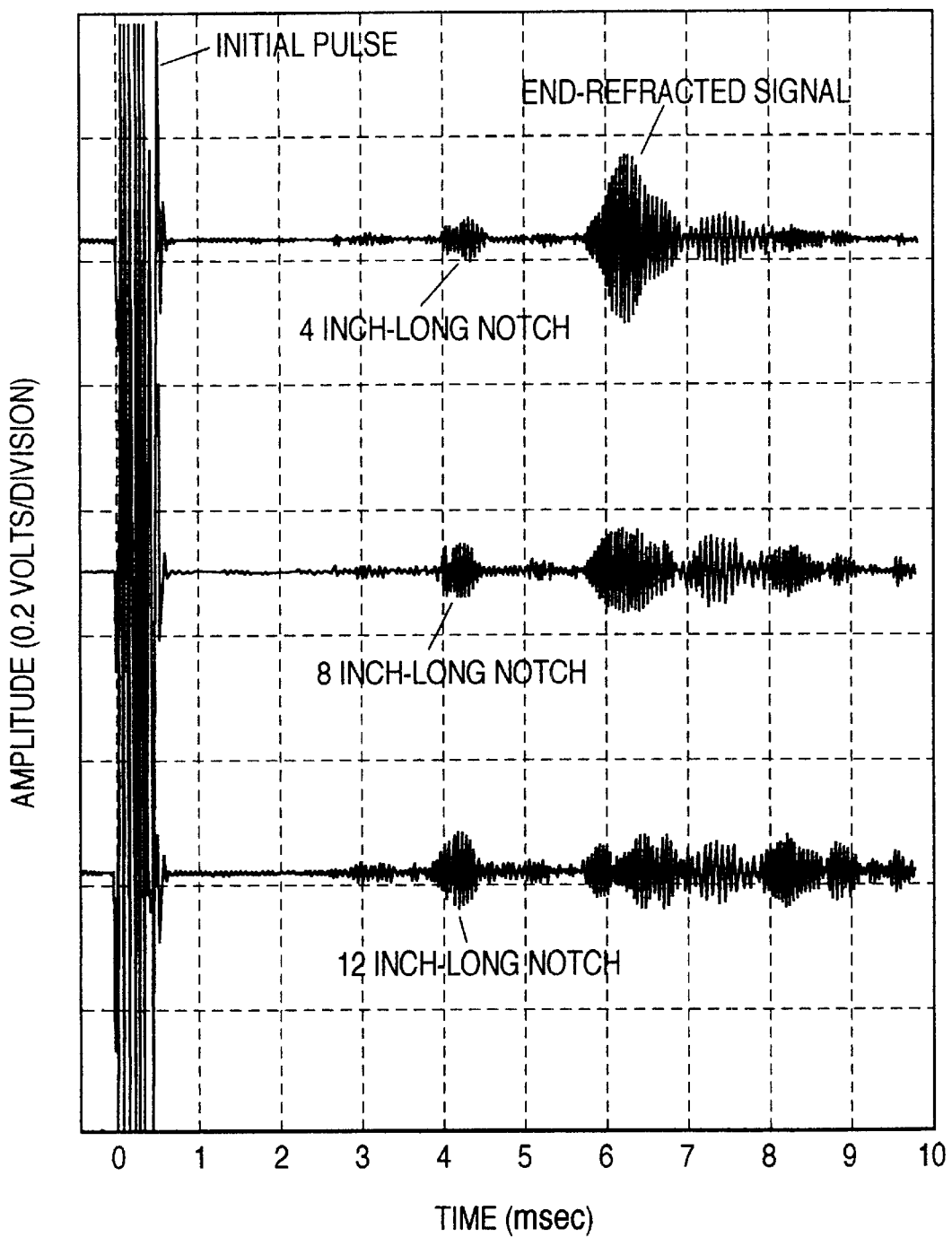
FIG. 7 is a plot of three signals received through the system of the present invention utilizing a 20 kHz anti-symmetric ($A_0$) wave mode signal in a 4 foot wide, 20 foot long, 0.25 inch thick steel plate.

Examples of such signals are shown in FIGS. 6 and 7. FIG. 6 shows pulse-echo magnetostrictive sensor data for a 40 kHz $S_0$ wave mode signal obtained in a 4 foot wide, 20 foot long, 0.25 inch thick steel plate. Three signals are shown for data collected with a 4 inch long, 8 inch long, and 12 inch long notch cut in the plate at a point approximately two-thirds of the length of the plate away from the sensor.

FIG. 7 shows pulse-echo magnetostrictive sensor data for a 20 kHz $A_0$ wave mode signal obtained in a 4 foot wide, 20 foot long, 0.25 inch thick steel plate. Three signals are also shown for data collected with a 4 inch long, 8 inch long, and 12 inch long notch cut in the plate at a point approximately two-thirds of the length of the plate away from the sensor.

In each case, the notch is not only detectable but may be characterized as to size and position. Various signal analysis techniques may be applied to these signals to discern and characterize other types of anomalies found in such plate-type structures. Discrete fractures and the like are typically identified by isolated reflected waves, while broad deteriorations or corrosions in the plate might be identified by grouped waves received over a period of time. In addition, it is anticipated that signature signals of a particular plate type structure might be acquired prior to implementation of the structure into service. In this manner subsequent signatures may be acquired periodically and compared with the initial base line reference signature to determine the presence of developing anomalies within the plate.

To prove the invention works, symmetric ($S_0$) and antisymmetric ($A_0$) longitudinal wave mode signals were generated and detected using a 12 inch long magnetostrictive probe such as shown in FIG. 2. To generate and detect these wave modes, the bias magnets 36 and 38 are applied in the direction parallel to the direction of wave propagation (perpendicular to the lengthwise length of the magnetostrictive probe). The same probe as shown in FIG. 2 can be used to generate and detect shear horizontal waves in a plate by applying DC bias magnetic fields in a direction perpendicular to the wave of propagation (or parallel to the lengthwise direction of the magnetostrictive probe).

Figure 8A:
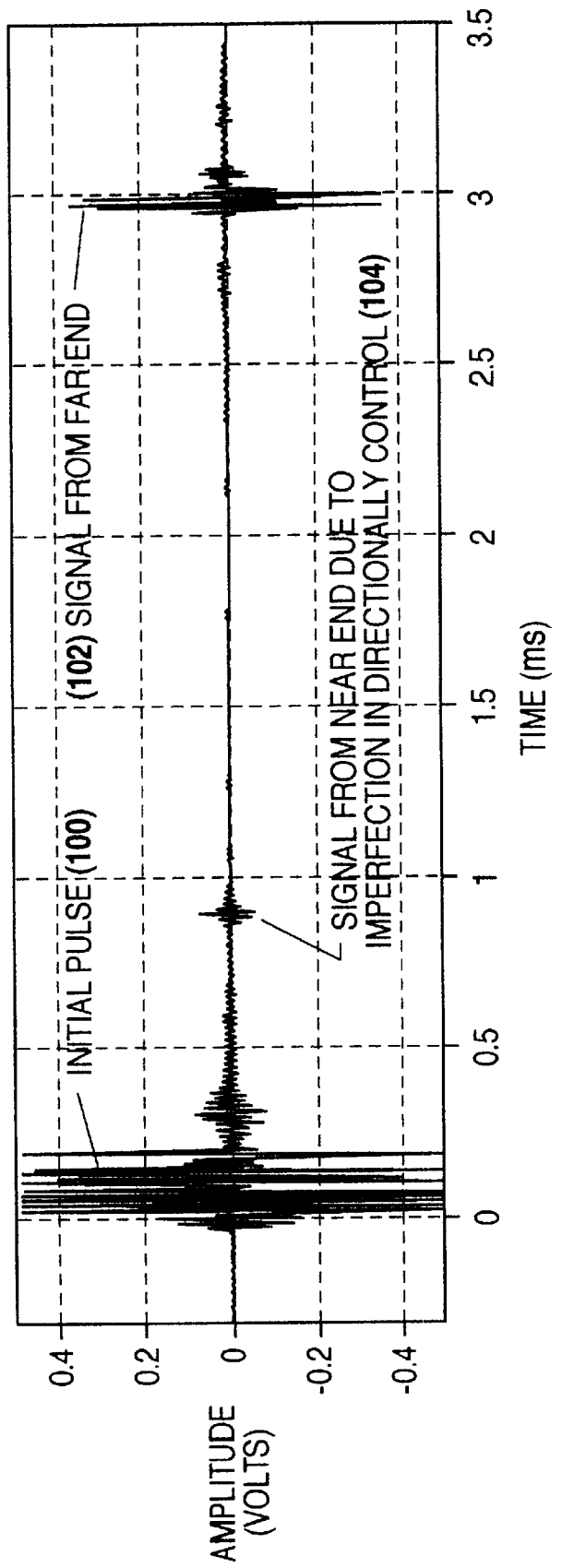
FIGS. 8(a) and (b) are plots of a shear horizontal (SH) wave received through the system of the present invention utilizing an 80 kHz wave in a 4 foot wide, 20 foot long 0.25 inch thick steel plate, before and after a 0.05 inch hole is cut therein.

Using a 4 inch long magnetostrictive probe, a signal was induced in a 0.25 inch thick, 4 foot wide, 20 feet long, steel plate. FIG. 8(a) shows the signal as generated and reflected over time. The initial pulse 100 is generated by the magnetostrictive transmitter controller 12 until it reaches the far end of the sheet and a signal from the far end 102 is received by the receiver coil/core 20. A signal from the near end 104 is received due to the imperfect directionality control of the system.

After drilling a 0.25 inch hole about two-thirds of the way down the sheet, another initial pulse 100 is sent down the sheet. Again, a signal is received from the near end 104 due to imperfect directionality control. Also, a signal 102 from the far end is received. However, now a signal 106 is received that indicates the 0.25 inch hole in the sheet. Therefore, FIGS. 8(a) and (b) in combination clearly illustrate that shear horizontal waves can be used in the magnetostrictive inspection techniques and probes of the current invention. Also, the magnetostrictive testing of the large plate structures is a suitable for low frequency operation (200 kHz or less), has good sensitivity and long range inspection, and is relatively tolerate to liftoff. This is not the case if the inspection technique had used other common nondestructive evaluation techniques, such as electromagnetic acoustic transducers.

Figure 9:
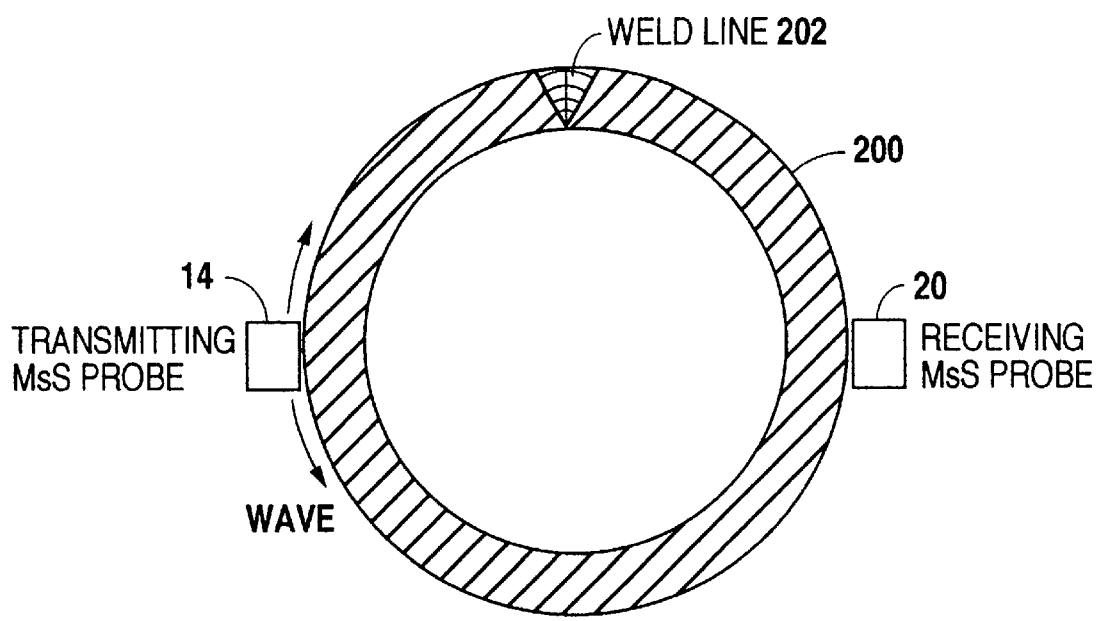
FIG. 9 is a pictorial end view of a welded pipe being inspected using a magnetostrictive transmitting probe and a magnetostrictive receiving probe on opposite sides of the pipe for transmission and receipt of Lamb or SH waves.
Figure 10A:
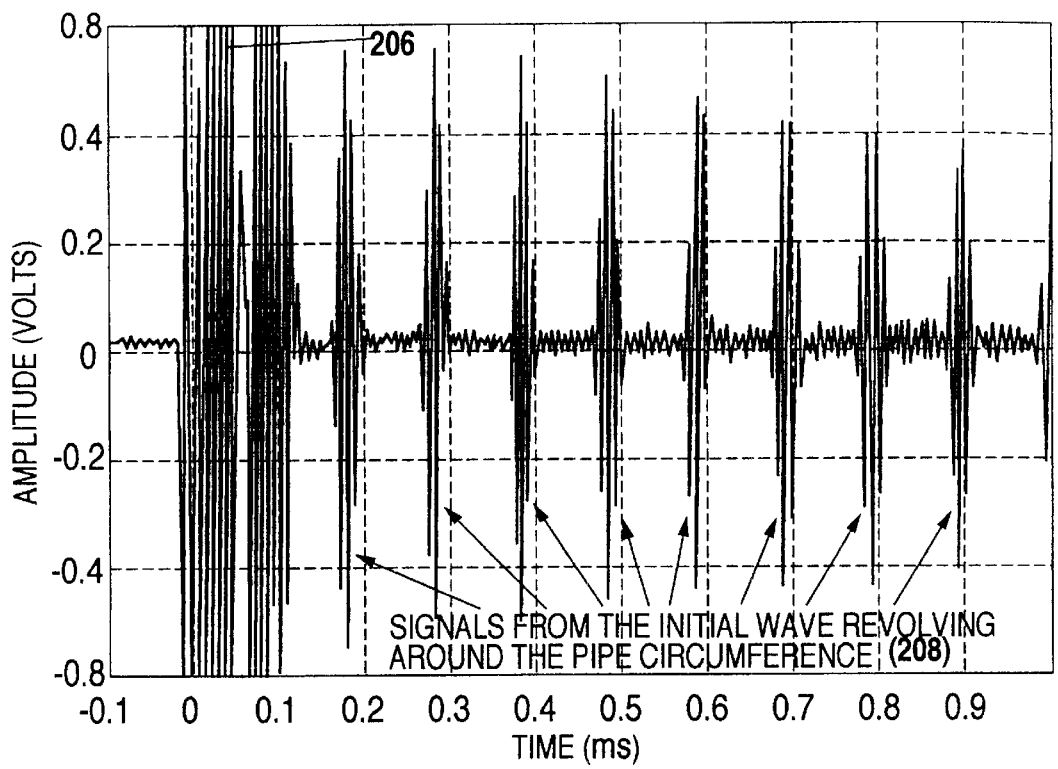
FIGS. 10(a) and (b) are plots of signals received through the system of the present invention when used to test a pipe as shown in FIG. 9, utilizing a 150 kHz SH wave mode in a 4.5 inch outside diameter steel pipe having a 0.337 inch thick wall before and after cutting a notch therein.

Pipes can be considered as plates that are simply bent in a circle. Pipes are literally made from sheet metal that is bent into a circle and welded on one side thereof utilizing electric resistance welding. Magnetostrictive inspection techniques may be used to inspect such pipes as shown and explained in connection with FIG. 9, including the electric resistance welding. A pipe 200 is shown with a weld line 202. A transmitter coil/core 14 is located on one side of the pipe 200 and a receiver coil/core 20 is located 180° on the opposite side of the large diameter pipe 200. While not shown, magnetic bias is provided adjacent to the transmitter coil/core 14 and the receiver coil/core 20. Using the inspection system 10 as shown in FIG. 1, an initial pulse 206 is started around the pipe as shown in FIG. 10(a). Each time the pulse passes the receiver coil/core 20, a signal 208 is received. The signal 208 dies out over a period of time and after repeated revolutions around the pipe 200.

If the transmitter coil/core 14 is 180° around the pipe 200 from the receiver coil/core 20, the two opposite going waves add constructively producing a single large amplitude signal. Once generated, the initial pulse 206 keeps revolving around the circumference of the pipe 200 until all of its energy is dissipated. Therefore, the generated wave produces signals at regular intervals which are equal to the transient time of the shear horizontal wave to travel around the full circumference of the pipe 200. If there are any defects at the weld line 202, they will clearly be indicated as defect signals. If the weld line is approximately 90° from transmitter coil/core 14, then the defect would be approximately midway between the signals 208 as received by the receiver coil/core 20.

To prove the measuring of the defects, the applicant, after measuring the signal as shown in FIG. 10(a), cut a notch in the pipe 200. The test was then repeated with an initial pulse 206 inducing a shear horizontal wave around the circumference of the pipe 200. Again, signals 208 indicate each time the shear horizontal wave reaches the receiver coil/core 20. However, in addition, there are notch signals 210 that are created by a reflected signal from the notch that has been induced in the pipe 200. The notch signal 210 increases in amplitude with time because each time the initial wave revolves around the pipe 200, it passes the notch defect thereby producing a notch defect signal 210 which is then added to the previous notch defect signal 210. The increasing of the notch signal 210 occurs for a period of time and then it will decrease until its energy is dissipated, the same as signal 208.

Figure 10B:
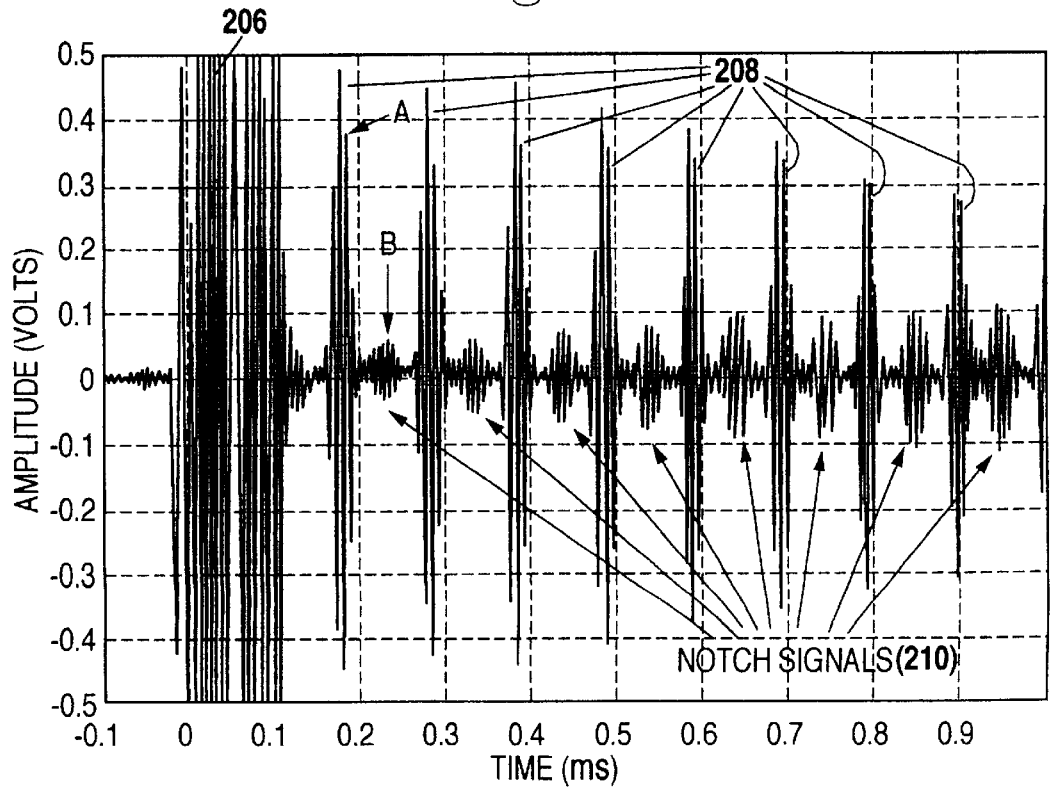

It is possible to get a comparative indication as to the size of the defect by the ratio between the first initial wave signal amplitude 208 and the first defect signal amplitude 210. In the example illustrated in FIG. 10(b), the notch is approximately 8% of the cross-sectional area. This compares well to the ratio of signal 208 to 210 being approximately 10%. This is intended to be a rough generalization as to the size of the notch. Obviously, other factors would be considered, such as whether the notch is perpendicular or parallel to the direction of travel of the shear horizontal wave.

By use of the method as just described, the present invention can be used to inspect pipes for longitudinal defects and corrosion defects. In the present method, the magnetostrictive probes are moved along the length of pipe to determine any defects in the pipe. In manufacturing facilities, the magnetostrictive transmitters or receivers may be stationary with the pipes moving therebetween and simultaneously being inspected for any defects.

While one of the advantages of the present invention is the ability to carry out broad inspections of large volumes of a plate type structure from a single positioning of the sensor, it is anticipated that the complete investigation of a containment vessel or the like would require multiple placements of the sensor in a variety of positions and orientations. For example, a containment vessel might require the placement of the sensor in a sequential plurality of positions along a predetermined scan line (which could be either horizontal or vertical to the floor) that best achieves the inspection of the entire structure. In this manner, a progressive inspection of an entire containment vessel is carried out without the requirement that all surfaces of the vessel be accessed.

Figure 11:
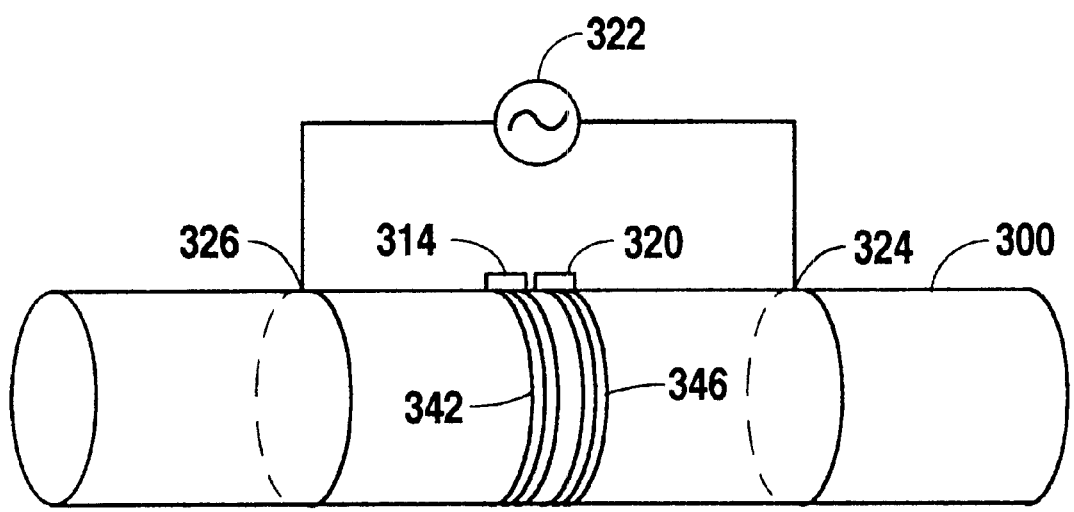
FIG. 11 is a pictorial view of a pipe being inspected using a magnetostrictive transmitting probe and a magnetostrictive receiving probe for transmission and receipt of torsional waves with a high DC electric current for circumferential magnetization.

FIG. 11 is a pictorial view of a pipe 300 being inspected using a magnetostrictive transmitter 314 and a magnetostrictive receiver 320 on the pipe 300 for transmission and receipt of torsional waves. A current source 322 is applied to the pipe 300 at contact points 324 and 326 that connect around the entire pipe 300. The current source 322 can be either a DC source or a low frequency AC (approximately 10 Hz).

At a given frequency, more than one longitudinal (L) wave mode can exist in a pipe or tube. The defect detectability of the MsS technology has been found to be hampered by the presence of extraneous wave modes that were produced by the MsS itself and/or by mode conversion of the transmitted wave at geometric features in pipelines, such as welds, elbows and tees. In addition, when the pipe 300 under inspection is filled with a liquid, the liquid interacts with the L-wave mode and causes many extraneous signals to be produced, which can significantly degrade defect detectability.

In order to overcome these deficiencies in detecting defects in pipes or tubes containing a liquid, a torsional wave is used for the inspection. The torsional wave is a shear wave that propagates along the length of the pipe 300 or tube. Because the torsional wave is a shear wave in a pipe or tube, its interaction with a liquid is negligible (unless the liquid is viscous). Therefore, the defect detectability of torsional waves will not be hampered by the presence of liquid in the pipe 300. In addition, the torsional wave exists as a single mode up to a considerable frequency and, consequently, has minimal problems in defect detectability due to the presence of extraneous wave modes. The torsional wave therefore is expected to have significantly better defect detectability than the longitudinal wave modes.

Figure 13A:
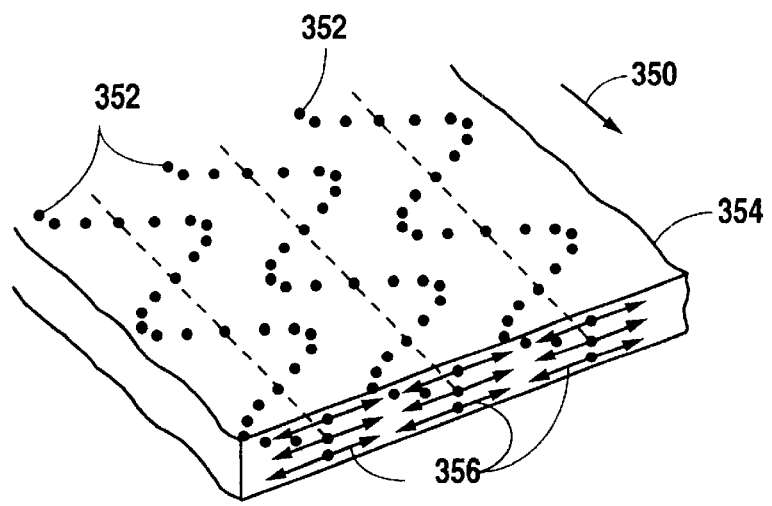
FIG. 13 is an illustration of different types of magnetostrictive waves in a plate to illustrate dimensional changes in the plate.

To explain why a torsional wave would not be hampered by the presence of liquid in pipe 300, an explanation of the dimensional changes in the material due to magnetization and the waves generated therefrom is provided in conjunction with FIG. 13. Referring to FIG. 13, the larger arrows 350 shown in FIGS. 13a, b and c represent the direction of propagation of the wave front. Referring to FIG. 13a, the dotted lines 352 give an exaggerated representation of the dimensional changes in the ferromagnetic plate 354 when a shear wave is projecting in direction 350. Arrows 356 represent the oscillations occurring by the dimensional changes illustrated by waves 352. For the purposes of illustration, the dimensional changes due to magnetization caused by waves 352 and illustrated by arrows 356 have been exaggerated.

Figure 13B:
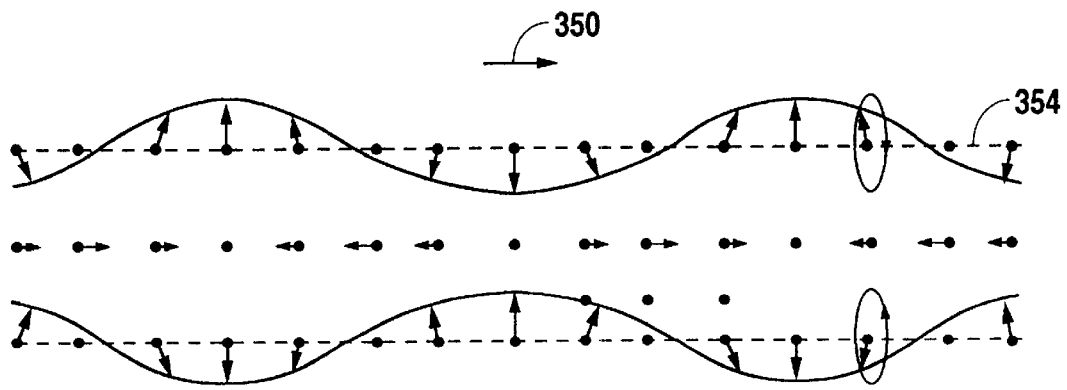
Figure 13C:
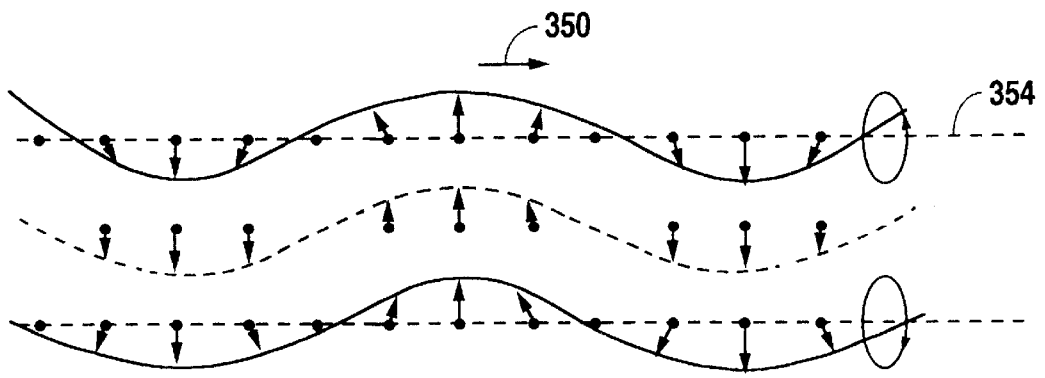

Referring to FIGS. 13b and 13c, Lamb waves are projecting along the ferrogmagnetic plate 354. In FIG. 13b, the dimensional changes due to a symmetrical Lamb wave propagating in direction 350 is illustrated in an exaggerated form. The smaller arrows shown in FIG. 13b represent the dimensional changes of the plate 354. FIG. 13c shows an asymmetrical Lamb wave that would propagate along plate 354, again with the small arrows representing dimensional changes of the plate 354. As can be seen in FIG. 13, the dimensional changes in the Lamb waves shown in FIGS. 13b and 13c will react against any liquid contained in a pipe or container. However, the use of a shear wave or a torsional wave as shown in FIG. 13a, because the dimensional change is in the same plane of the plate 354, there would be no reaction or interference by the liquid contained in any pipe or container. Therefore, the shear or torsional wave is the ideal waveform to use if the plate or pipe is being checked that may contain a fluid.

As illustrated in FIG. 11, coil windings 342 and 346, transmitter 314 and receiver 320 that are used in the existing MsS L-wave inspection are installed around pipe 300. A high ampere electric current is applied to pipe 300 by current source 322 applied at contact points 324 and 326 along the length of pipe 300. The electric current flowing along pipe 300 sets up a DC bias magnetization in the circumferential direction of the pipe 300 necessary for MsS generation and detection of torsional waves in the wall of pipe 300. The generated torsional waves propagate along the length of pipe 300, and signals reflected from defects in pipe 300 are detected in the same manner used for L-wave pipe inspection. The results of experimentation on this aspect of the invention are contained in FIG. 12.

FIGS. 12a–c are plots of signals received through the system of the present invention utilizing torsional waves when used to test pipe 300 filled with water shown in FIG. 11. The data were obtained using a 32 kHz torsional wave mode in a 4.5 inch outside diameter steel pipe having a 0.337 inch thick wall and 168 foot length. The sample contained several simulated defects. The DC current applied was approximately 150 amps, and the frequency of the MsS was 32 kHz. Signals from small simulated defects (whose cross sections were about one percent of the total pipe 300 wall cross section) were not recognizable in these data. It is however expected that the application of a higher DC current would permit detection of the small defects. The data showed no effects of water.

Referring to the waveform shown in FIGS. 12b and 12c, numerals 1 through 12 represent the defects that occur in the pipe. The MsS transmitter 314 and receiver 320 along with coil windings 342 and 346 are located at 54 feet down the pipe 300 from one end represented by end F1. The other end of the pipe is represented by end F2. There are three welds in the pipe represented by W1, W2 and W3, respectively, at 42 feet, 84 feet, and 126 feet. When the torsional wave is propagated down the pipe towards end F2, there will be some small amount of reflection of the signal from end F1 because of imperfect direction control as can be seen in FIG. 12b. Likewise, when the waveform is propagated towards end F1, there is some reflection of the signal from end F2 as shown in FIG. 12c. Therefore, in FIG. 12b, the torsional wave signal is first directed towards end F2. In FIG. 12c, the signal is directed towards end F1. Also, as can be seen in the signals, some of the simulated defects are so small they can hardly be distinguished. Other simulated defects that are larger in cross-sectional area can be seen in the reflected signals shown in FIGS. 12b and 12c.

Figure 14:
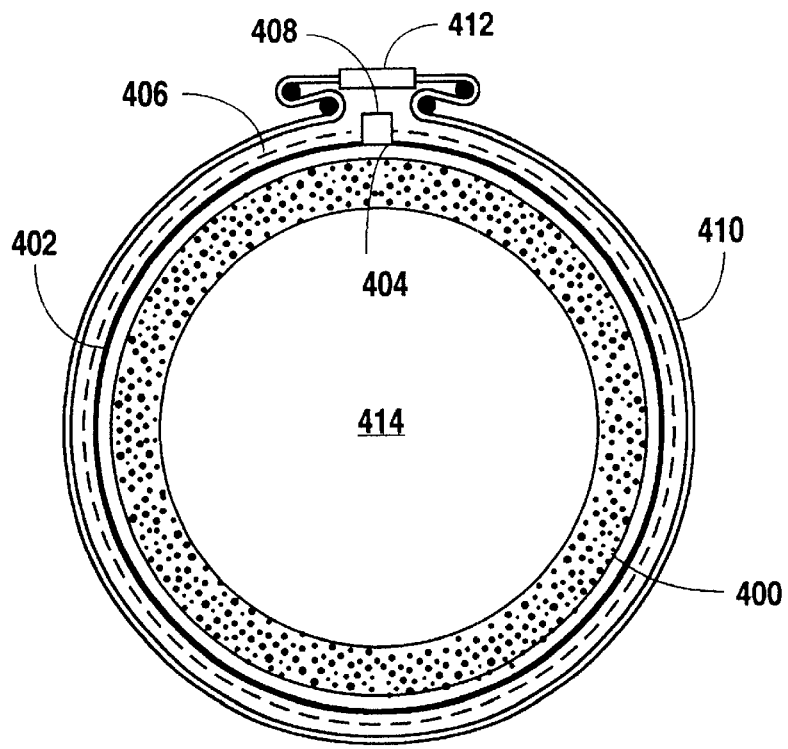
FIG. 14 is a cross-sectional view of a transmitter or receiver attached to a pipe for transmission or receipt of torsional waves.

Referring now to FIG. 14, an alternative way of creating the circumferential magnetic field in a pipe 400 is illustrated. Wrapped around the pipe 400 is a ferromagnetic strip 402 that contains residual magnetization. The ferromagnetic strip 402 would typically be about an inch wide and wrapped almost around pipe 400, with the exception of a small gap 404 at one end thereof. The ferromagnetic strip 402 may be made from any material that has good magnetization characteristics, such as nickel, grain-oriented silicon steel, or a magnetostrictive material, such as TERFENDOL-D®. The objective is to have a flexible strip of material that has good magnetization characteristics (ability to retain residual magnetization and high magnetostrictive coefficient) for wrapping around pipe 400. The residual magnetization in the ferromagnetic strip 402 is induced prior to wrapping around the pipe 400 by applying an external magnetic field to the ferromagnetic strip 402 and then removing the external field (not shown). After wrapping the ferromagnetic strip 402 around pipe 400, a magnetostrictive coil 406 is placed around the magnetized ferromagnetic strip 402. The coil 406 may be of the common ribbon type with a coil adapter 408 connecting the two ends of the ribbon type coil 406.

To press the magnetized ferromagnetic strip 402 against pipe 400, some type of external pressure is necessary. The embodiment shown in FIG. 14 is a flexible strap 410 wrapping around both ferromagnetic strip 402 and coil 406. The flexible strap 410 is pulled tight by means of buckle 412, which in turn presses the ferromagnetic strip 402 against the pipe 400. The guided waves are then generated in the ferromagnetic strip 402 and coupled into the pipe 400. For detection, the guided waves in the pipe 400 are coupled to the ferromagnetic strip 402, which guided waves are subsequently detected by the MsS coil 406 placed over the ferromagnetic strip 402.

For torsional wave generation and detection, the residual magnetization is induced along the lengthwise direction of the ferromagnetic strip 402. For longitudinal wave generation and detection, the residual magnetization is induced along the width of the ferrogmagnetic strip 402. The pressing on the ferromagnetic strip 402 provides a mechanical coupling of the guided waves between the pipe 400 and the ferromagnetic strip 402. The illustration as shown in FIG. 14 can be either a transmitter or a receiver of guided waves (either longitudinal or torsional wave modes) that are propagated along the pipe 400.

Figure 15:
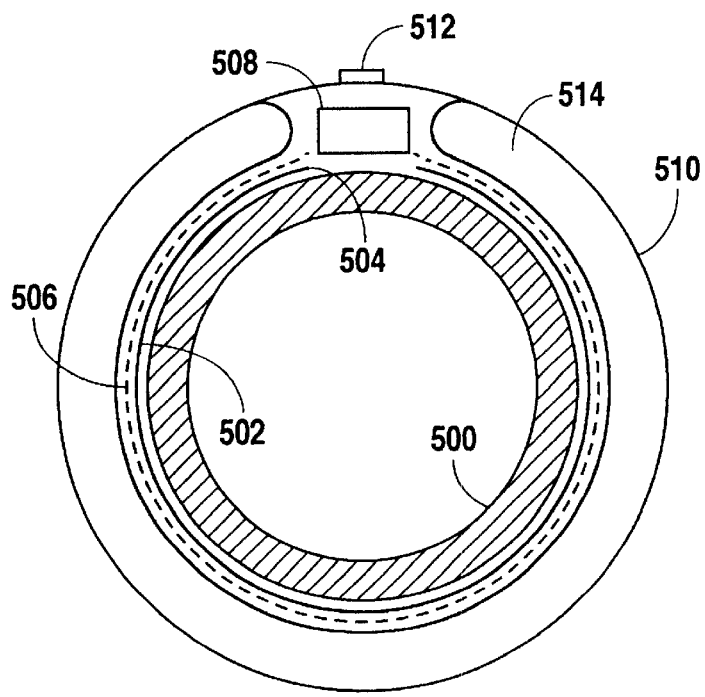
FIG. 15 is another embodiment of a cross-sectional view of a transmitter or receiver attached to a pipe for transmission or receipt of torsional waves.

Referring now to FIG. 15, another alternative is shown as to how to create a guided wave in pipe 500. Just as in FIG. 14, in FIG. 15, a magnetized ferromagnetic strip 502 is wrapped around the pipe 500. Again, a gap 504 will exist between two ends of the ferromagnetic strip 502. Also, the same as is the case in FIG. 14, a coil 506 is wrapped around the ferromagnetic strip 502, which coil 506 is of the ribbon type and connected by a coil adaptor 508. However, the means of applying pressure against the ferromagnetic strip 502 to press it against the pipe 500 is different in FIG. 15 from FIG. 14. In FIG. 15, a metal case or container 510 encircles the ferromagnetic strip 502 and coil 506. The metal case or container 510 is held together by clamp 512. Inside of the metal case or container 510 is located a pneumatic or hydraulic tube 514 that may be inflated. By inflating the tube 514, it presses the coil 506 and ferromagnetic strip 502 against the pipe 500. Again, the embodiment as just explained in conjunction with FIG. 15 may be used as either a transmitter or receiver of guided waves being propagated along pipe 500.

The width of the magnetized ferromagnetic strips 402 or 502 is adjusted depending on the frequency and the mode of the guided waves. For high frequencies, the magnetized ferromagnetic strips 402 or 502 should be narrower; for lower frequencies, the magnetized ferromagnetic strips 402 or 502 should be wider.

Figure 16:
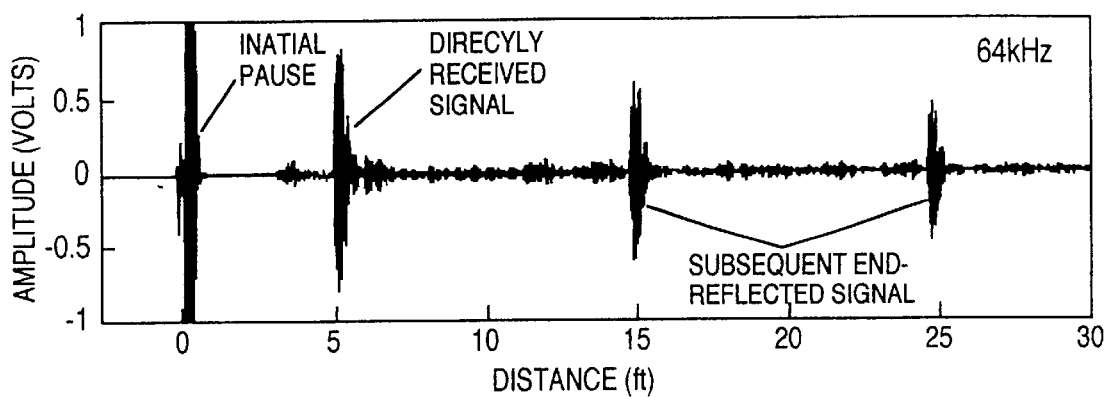
FIG. 16 is a plot of a signal received using the embodiment as shown in FIG. 14 on a 9.3 foot long pipe having 4 inch outside diameter and a 0.224 inch thick wall, with the transmitters and receivers being located on each end of the pipe.

The feasibility of the approach explained in FIGS. 14 or 15 has been proven in the laboratory as illustrated in conjunction with FIG. 16. Using a 4-inch outside diameter pipe with a 0.224 inch wall thickness pipe which was 9.3 feet long, a crude test was performed. The magnetized ferromagnetic strip 402 or 502 was made of 0.01 inch thick nickel foil. The magnetized ferromagnetic strips 402 or 502 were placed circumferentially around each end of the pipe sample. The magnetized ferromagnetic strips 402 or 502 were mechanically coupled to the outside surface of the pipe and in this case strapped using the method as shown in FIG. 14. FIG. 16 shows the data acquired at 64 kHz by transmitting the torsional wave from one end of the pipe and detecting the signals at the other end of the pipe. The data clearly indicates FIG. 14 as being an acceptable method for generating and detecting guided waves in pipes.

Figure 17:
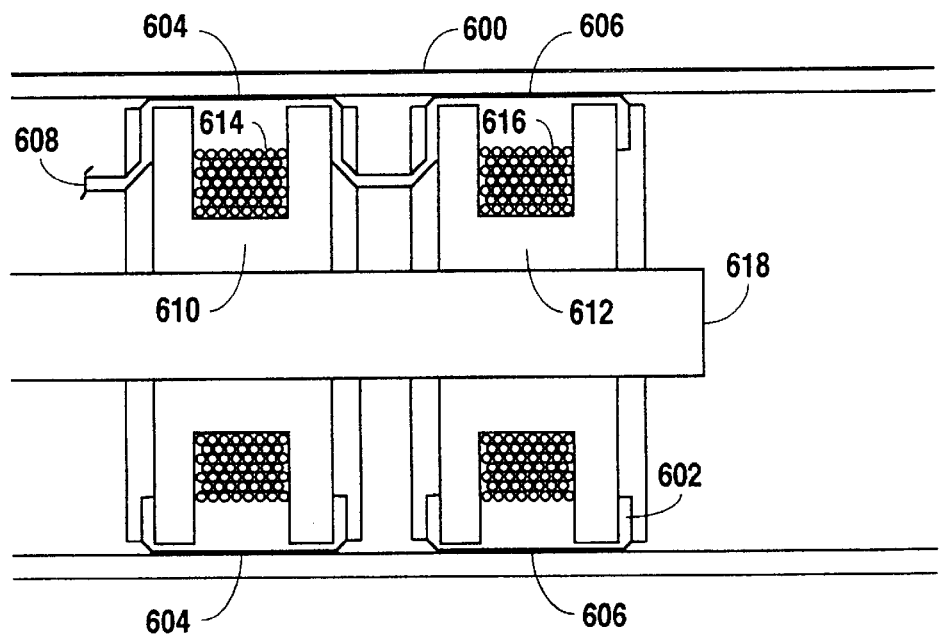
FIG. 17 is yet another embodiment of a cross-sectional view of a transmitter and receiver attached to a tube for transmission or receipt of torsional waves from inside the tube.

Referring to FIG. 17, a probe for generating and detecting guided waves in a tube 600 from inside the tube 600, which uses the same principle as the present invention, is illustrated. A pneumatic tire 602 has ferromagnetic strips 604 and 606 bonded therearound. In FIG. 17, ferromagnetic strips 604 and 606 represent a transmitter and a receiver, respectively, of the torsional waves. The pneumatic tire 602 has a pressure valve 608 for inflating/deflating.

Inside of the pneumatic tire 602 are two bobbin type cores 610 and 612 about which a transmitting coil 614 and receiving coil 616 are wound, respectively. To hold everything together in their respective locations, the cores 610 and 612 are mounted on rod 618.

By inflating the pneumatic tire 602 through pressure valve 608, the magnetized ferromagnetic strips 604 and 606 are pressed against the inside of tube 600. Thereafter, the guided wave generated by transmitting coil 614 in the ferromagnetic strip 604 is coupled to the tube 600 and propagates along the tube 600. Reflected signals from defects in tube 600 are received back through the ferromagnetic strip 606 and detected by receiving coil 616. The type of signal that will be generated will be a guided wave that propagates along tube 600. It is envisioned that the configuration as shown in FIG. 17 will be inserted in the end of a tube 600 to propagate a signal down the entire length of the tube to detect flaws or defects that may exist in the tube 600. The cores 610 and 612 are ferrite or ferromagnetic steel to aid in the transmission and receiving of magnetostrictive signals to and from the tube 600.

Figure 18:
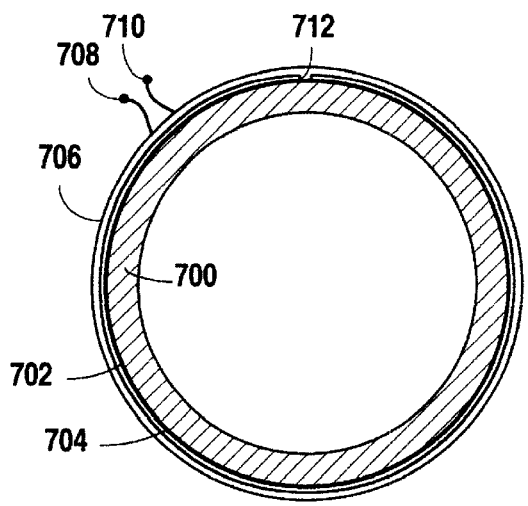
FIG. 18 is another embodiment of a cross-sectional view of a transmitter or receiver attached to a pipe for transmission or receipt of torsional waves.

Another embodiment of the present invention that has been found useful for either short term inspection or long term monitoring of pipelines is illustrated in the embodiment shown in FIG. 18. A pipe 700 has a thin ferromagnetic strip 702 attached to its outer surface by a suitable couplant 704. Wrapped around the outside of the thin ferromagnetic strip 702 is a coil 706 that has external connections 708 and 710.

As previously described in connection with FIG. 14, the thin ferromagnetic strip 702 is about one-half inch to one inch wide and has a gap 712 between the respective ends thereof. The thin ferromagnetic strip 702 may be made from any material that has good magnetization characteristics, such as nickel, grain-oriented silicon steel or a magnetostrictive material, such as TERFENDOL-D®. The thin ferromagnetic strip 702 should have the flexibility that it can be wrapped around the pipe 700. Also, it is important that the thin ferromagnetic strip 702 retain residual magnetization and have a high magnetostrictive coefficient.

The couplant 704 may vary depending upon whether the use is for a short term inspection or a long term monitoring. If the use is for short term inspection, the couplant 704 would be of a thick, highly viscous material, such as honey, that would stick the thin ferromagnetic strip 702 to the pipe 700. Also, the coil 706 would have a coil adapter (similar to those described in connection with FIGS. 14 and 15) so that the coil 706 can be quickly removed. However, for the purposes of this illustration, assume that long term monitoring is desired. For long term monitoring, the couplant 704 would be made from a couplant that becomes a rigid material, such as epoxy, to physically bond the thin ferromagnetic strip 702 to the pipe 700. For long term monitoring, it is important that the couplant 704 maintain a good bond with the pipe 700 over an extended period of time.

The thin ferromagnetic strip 702, prior to placing on the pipe 700, has residual magnetization induced therein. Because a torsional wave is ideal for long term monitoring of a pipe, especially a pipe that may be filled with fluid, the residual magnetization in the thin ferromagnetic strip 702 is induced in the lengthwise direction of the thin ferromagnetic strip 702. Thereafter, the thin ferromagnetic strip 702 is ready for bonding to the pipe 700 with the couplant 704. After bonding, the coil 706 is wrapped around the thin ferromagnetic strip 702, with the external connections 708 and 710 being available for monitoring.

Figure 19:
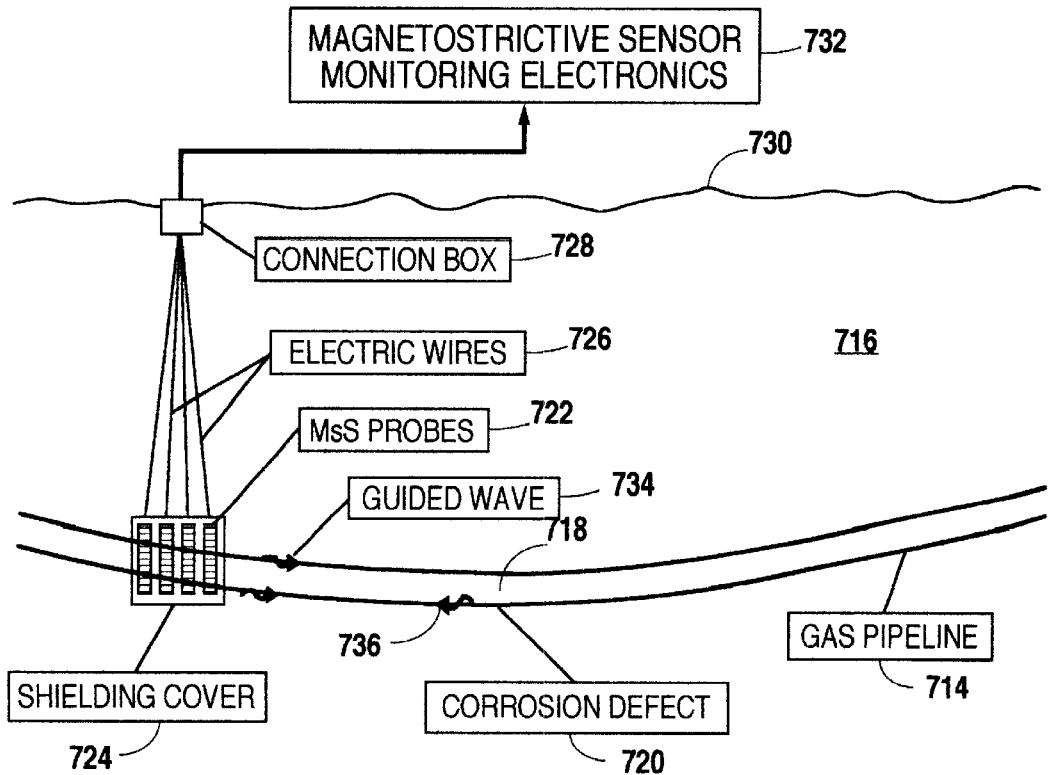
FIG. 19 is a pictorial diagram showing a use of the present invention for long term monitoring of a pipe.

An ideal situation for the use of the magnetostrictive sensor monitoring technology is involving gas pipelines. It has been found that gas pipelines have a tendency to accumulate fluids inside the gas pipeline along any low point in the gas pipeline, which fluid accumulation will tend to cause corrosion. Referring to FIG. 19, a gas pipeline 714 is buried under ground 716 so that a low point 718 exists in the gas pipeline 714. At the bottom of the low point 718 is a corrosion defect 720. If there is some way to monitor the low point 718 in the gas pipeline 714, the corrosion defect 720 can be determined before catastrophic results, such as explosion of the pipeline.

Some distance from the low point 718 (typically up to 50 feet), magnetostrictive probes 722 (similar to those described in FIG. 18) are mounted around the gas pipeline 714. At least two magnetostrictive probes have to be used, but to determine directionality, a minimum of four magnetostrictive probes are necessary to make use of phased array interference principals so that direction of the signals can be determined. In the present illustration as shown in FIG. 19, four magnetostrictive probes 722 are illustrated.

Because the magnetostrictive probes 722 are buried under ground 716, and may be left buried for long periods of time with just periodic monitoring, some type of shielding cover 724 is necessary to protect the magnetostrictive probes 722. Electrical wires 726 connect to a junction box 728 located at the surface 730 of the ground 716.

In actual use, periodically magnetostrictive sensor monitoring electronics 732, similar to that described in conjunction with FIG. 1, is connected to the junction box 728 at the surface 730. The magnetostrictive sensor monitoring electronics 732 generates a signal that is fed through the electric wires 726 to the magnetostrictive probes 722 that causes a guided wave 734 to propagate along the gas pipeline 714. If there is a corrosion defect 720 in the gas pipeline 714, a defect signal 736 will be reflected back to the magnetostrictive probes 722 for detection by the magnetostrictive sensor monitoring electronics 732 via the electric wires 726 and connection box 728.

This system as just described in conjunction with FIG. 19 is envisioned for use along low points of gas pipelines that need to be monitored on an infrequent basis, such as every six months. By use of a permanent reference signal and comparing future signals against the reference signal, very small changes due to corrosion can be detected. Using this technique, corrosion defects as small as 0.2 percent of the cross-sectional area of the gas pipeline 714 can be detected.

Figure 20:
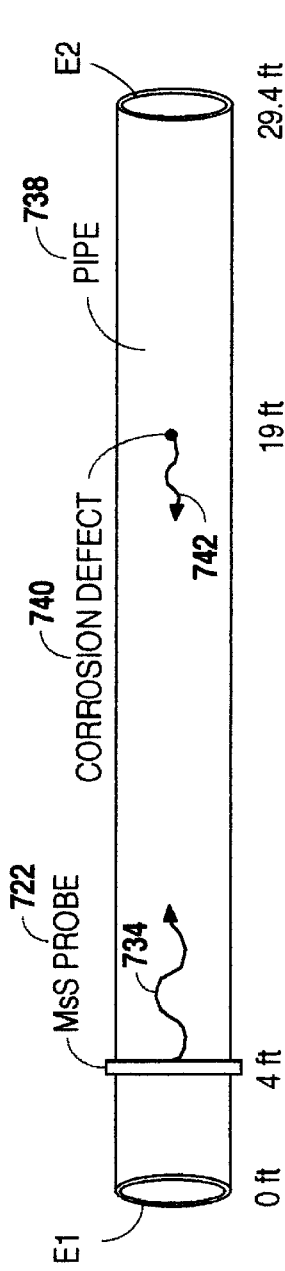
FIG. 20 is a pictorial view of the present invention as used on a test pipe.

This invention has been proven in the laboratory as will be explained in conjunction with FIG. 20 and the waveforms shown in FIGS. 21 and 22. A pipe 738 is shown that is 29.4 feet long and 4.5 inches in outside diameter having a 0.337 inch thick wall, each end being represented by E1 and E2. At 4 feet from E1 are located the magnetostrictive probes 722. The magnetostrictive probes 722 generate a guided wave 734 that propagates along the pipe 738. A corrosion defect 740 causes a reflected defect signal 742. The reflected defect signal 742 is 19 feet from end E1.

Figure 21:
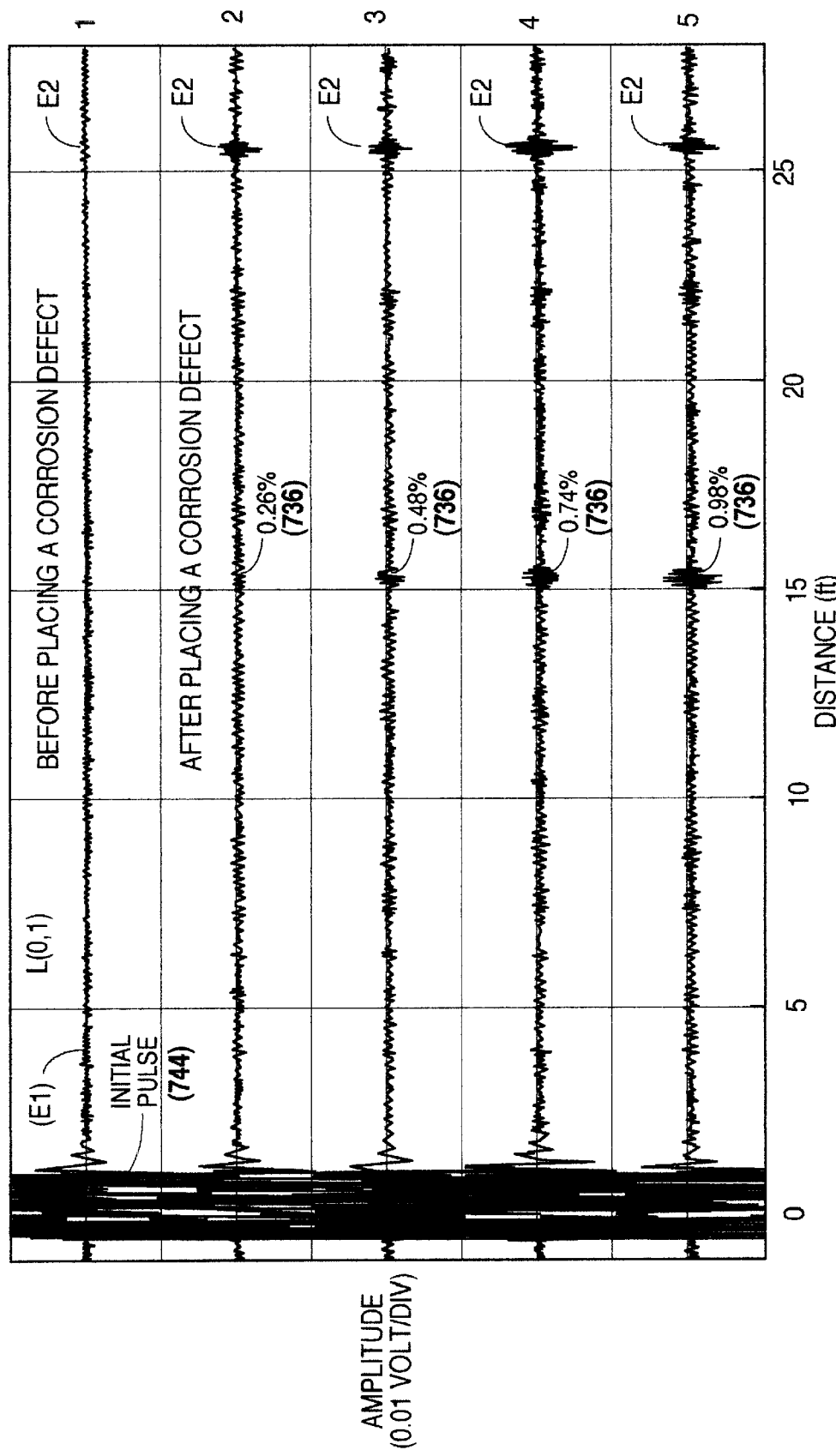
FIG. 21 is plots of signals received using the test pipe as shown in FIG. 20, using a differential algorithm.
Figure 22:
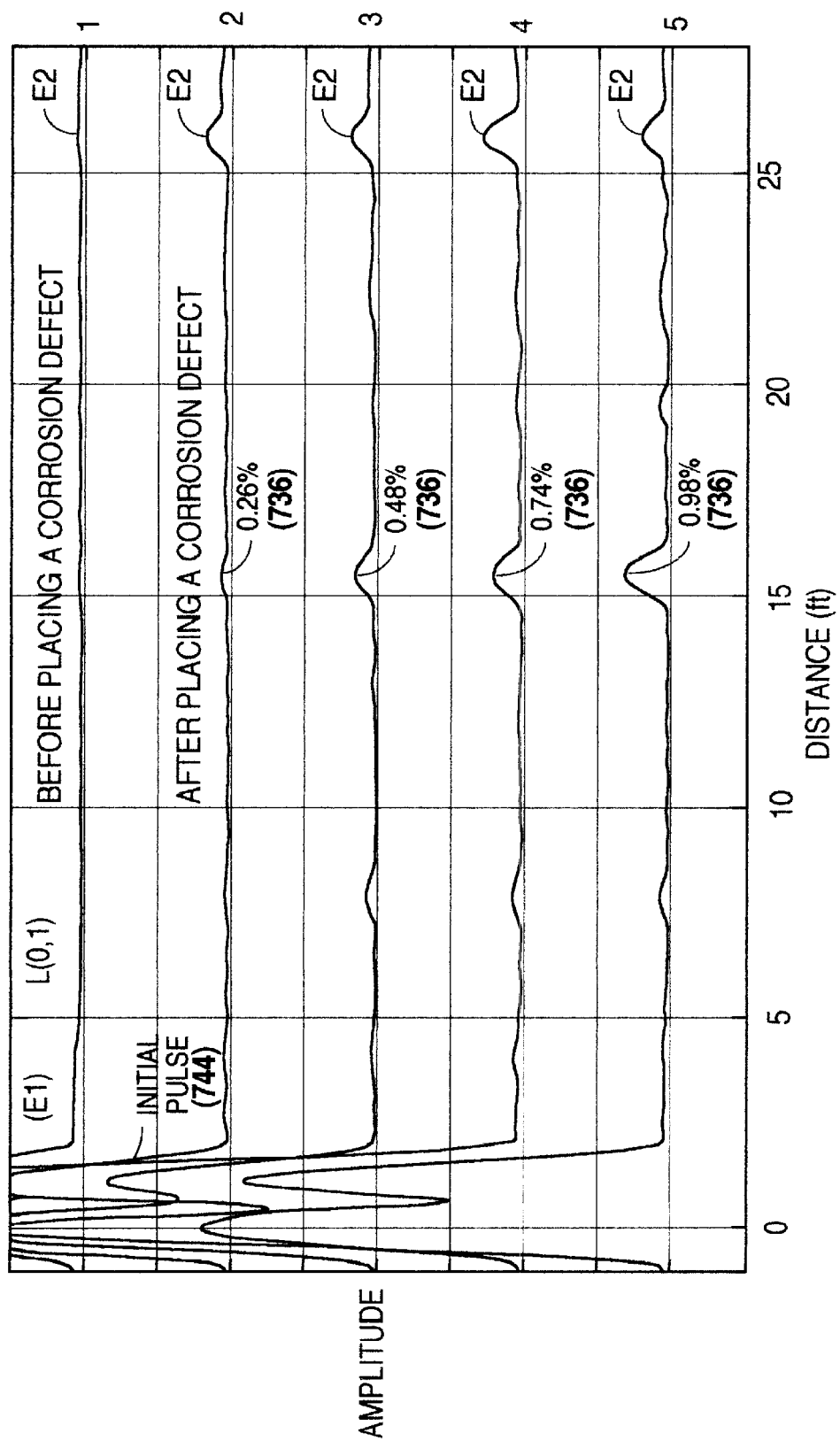
FIG. 22 is plots of signals received using the test pipe as shown in FIG. 20, using another type of differential algorithm.

Referring to FIG. 21, waveform 1 shows the result of subtracting the interference to form a waveform collected prior to any corrosion being applied. The reference signal subtracted from a second waveform obtained at a time different from when the reference signal is obtained is called the difference signal. An initial pulse 744 is applied to the pipe 738 and the directionality of the generated wave is controlled using electronics designed on phased array principals. The reflected end signals (E1 and E2) are canceled out because they are in both the reference and the waveform collected before any corrosion is applied. Then after applying a defect at corrosion defect point 740 that is approximately 0.26 percent of the cross-sectional area of the pipe wall, the difference signal is obtained for a 0.26 percent defect, the data shown in waveform 2 is obtained. This shows that the 0.26 percent defect signal 736 is just becoming detectable. Once the corrosion defect 740 is increased to 0.48 percent of the cross-sectional area, shown in waveform 3, the defect signal 736 is clearly detectable. By increasing the size of the corrosion defect to 0.74 percent of the cross-sectional area, the difference signal becomes even larger as shown in waveform 4. By the time the corrosion defect 740 reaches 0.98 percent of the cross-sectional area as shown in waveform 5, the defect signal 736 is clearly visible.

Also as the temperature of pipe 738 varies, the signal will travel at different speeds in the pipe. Therefore, when obtaining the difference signal, sometimes there is not a perfect match in the two signals due to the difference of speed of the signal moving along the pipe 738 caused by temperature changes. Referring to FIG. 21, the end signals E2 begin to increase in waveforms 2–5 due to the temperature change. However, for buried pipelines as illustrated in FIG. 19, the temperature underground is relatively constant and is close to the average mean temperature for the area.

To give an even clearer indication as to a defect, certain processing can be applied to the waveforms as shown in FIG. 21. For example, the signal can be squared and then averaged over a short window of time to give waveforms 1–5 as shown in FIG. 22. In this manner, the difference signal for the defect signal 736 is even clearer. The difference signal 736 becomes detectable at slightly over 0.2 percent loss of the cross-sectional area of the pipe being monitored.

By use of the techniques as just described in conjunction with FIGS. 18–22, detection of defects can occur in pipes other than ferromagnetic pipes. For example, the pipe could be plastic with the torsional wave being transmitted to the plastic pipe through the coupling. In other words, the torsional wave set up in the thin ferromagnetic strip 702 is transferred to any type of pipe 700 as long as the pipe is rigid with a high modulus of elasticity.

Figure 23:
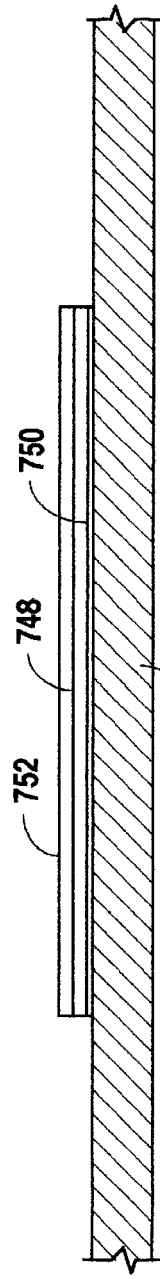
FIG. 23 is a cross-sectional view of the embodiment shown in FIG. 18 as applied to a plate.
Figure 24:
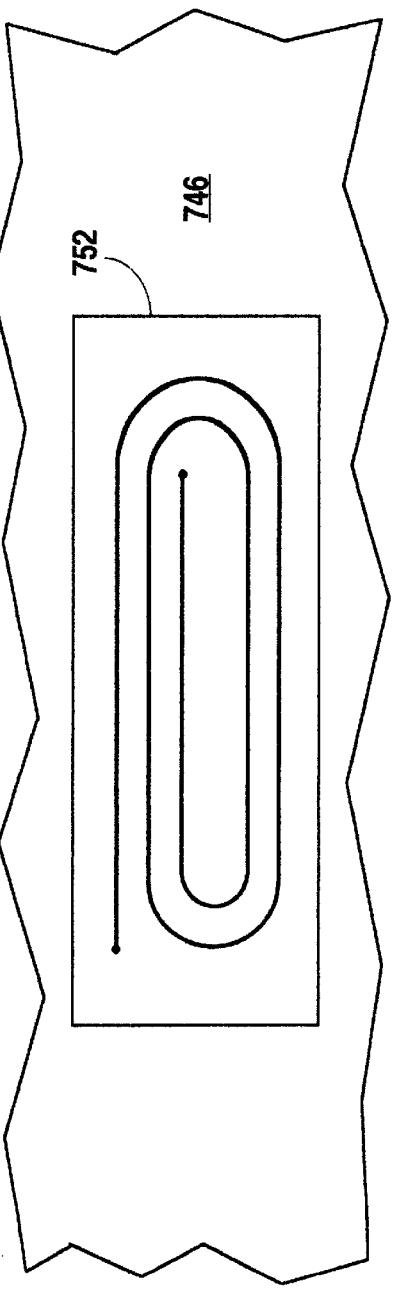
FIG. 24 is a top view of FIG. 23.

The same principle can be used for plate-type structures as is shown in conjunction with FIG. 23. A plate 746 has a thin ferromagnetic strip 748 coupled thereto by a couplant 750. Again, the thin ferromagnetic strip 748 may be of nickel or other materials described in conjunction with FIG. 18. On top of the thin ferromagnetic strip 748 is located a plate magnetostrictive probe 752. The plate magnetostrictive probe 752 could be either the type illustrated in FIG. 2 or a coil laid on a printed circuit board as illustrated in FIG. 24.

The couplant 750 is made from any thick material that will couple the thin ferromagnetic strip 748 to the plate 746. If a permanent monitoring feature is desired, the couplant 750 would be made from a coupling material that becomes rigid, such as epoxy. However, if it is desirable to periodically inspect the plate 746, and thereafter remove the magnetostrictive probe, the couplant 750 may be made from a thick viscous material, such as honey. However, other types of thick viscous material that will allow the magnetostrictive probe to be removed can be used.

The guided wave to be used in conjunction with FIGS. 18–22 for piping applications is a torsional wave. The guided wave to be used for plate-type structures would be a shear horizontal wave. The method and apparatus as described in conjunction with FIGS. 18–23 may be used not only to detect corrosion, but can also be used to detect transient stress signals due to vibration, cracking or mechanical impacts (for example, crash event of a passenger car for air bag operation). By use of the system as just described, it is inexpensive to implement by the end user.

Although a description of a preferred embodiment of the apparatus and method of the present invention has been described, it is anticipated that variations in the manner in which the basic sensor structure of the present invention may be utilized are possible. No specific dimensions for the sensor structure described have been identified as such would be dependent upon the specific plate type structures to be investigated. It is anticipated that sensors of a variety of lengths could be utilized depending upon the requirements of the environment of investigation. It is anticipated that other applications of the basic sensor structure described herein will be discerned by those skilled in the art of nondestructive evaluation of materials.

What is claimed is:

1. A method of nondestructive, short term inspection or long term monitoring of a structure to determine if said structure (a) has a defect such as a crack, corrosion or erosion or (b) has a transient stress signal due to vibrations, cracking or mechanical impacts, said method comprising the following steps:
   preparing a plurality of thin strips of ferromagnetic material of appropriate width and length;
   inducing residual magnetization along said length of said thin strips by applying an external magnetic field and thereafter removing said external magnetic field;
   coupling said thin strips in parallel to said structure;
   installing a magnetostrictive probe on each of said thin strips;
   generating a pulse signal in a transmitter control circuit and delivering said pulse signal to a first of said magnetostrictive probes to create guided waves in a first of said thin strips, which guided waves are coupled to said structure for propagation therein;
   magnetostrictively detecting any reflected waves by a second of said magnetostrictive probes in combination with a second of said thin strips, said reflected waves being coupled from said structure to said second of said thin strips; and
   determining if said reflected waves are due to said defect or said transient stress signal.

2. The method of nondestructive, short term inspection or long term monitoring of said structure as recited in claim 1 wherein said coupling step includes bonding said thin strips to said structure.

3. The method of nondestructive, short term inspection or long term monitoring of said structure as recited in claim 2 wherein said guided waves are shear waves.

4. The method of nondestructive, short term inspection or long term monitoring of said structure as recited in claim 2 wherein said structure is a pipe and said guided waves are torsional waves.

5. The method of nondestructive, short term inspection or long term monitoring of said structure as recited in claim 1 wherein said coupling step includes using a thick, viscous material as a couplant.

6. The method of nondestructive, short term inspection or long term monitoring of said structure as recited in claim 4 wherein said determining step includes storing a reference reflected wave and, after an appropriate period of time, repeating said generating step and said magnetostrictively detecting step, comparing a second reflected wave with said reference reflected wave to determine if defects have occurred during said appropriate period of time.

7. The method of nondestructive, short term inspection or long term monitoring of said structure as recited in claim 6 wherein said determining step includes subtracting said reference reflected wave from said second reflected wave.

8. The method of nondestructive, short term inspection or long term monitoring of said structure as recited in claim 1 wherein said determining step includes storing a reference reflected wave, thereafter repeating said generating step and said magnetostictively detecting step and comparing subsequent reflected waves with said reference reflected wave to determine if said transient stress signal has occurred.

9. The method of nondestructive, short term inspection or long term monitoring of said structure as recited in claim 8 wherein said reference reflected wave is continually updated.

10. The method of nondestructive, short term inspection or long term monitoring of said structure as recited in claim 1 wherein said thin strip may be selected from the group of ferromagnetic materials having appropriate magnetostrictive coefficients consisting of nickel, grain-oriented silicon steel or TERFENDOL-D®.

11. The method of nondestructive, short term inspection or long term monitoring of said structure as recited in claim 5 wherein said couplant is honey.

12. An apparatus for nondestructive, short term inspection or long term monitoring of a structure to determine if said structure (a) has a defect, such as a crack, corrosion or erosion, or (b) has a transient stress signal due to vibrations, cracking or mechanical impact, said apparatus comprising:
   a plurality of thin ferromagnetic strips that have residual magnetization therein, said thin ferromagnetic strips being coupled in parallel to said structure;
   a transmitter coil being located adjacent to a first of said thin ferromagnetic strips;
   a receiver coil being located adjacent to a second of said thin ferromagnetic strips;
   a transmitter control circuit connected to said transmitter coil for generating a pulse signal and delivering said pulse signal to said transmitter coil, said transmitter coil creating magnetostrictively a guided wave that is coupled from said first thin ferromagnetic strip to said structure to propagate along said structure;
   said receiver coil magnetostrictively detecting said guided wave and any reflected signals, including any caused by defect or transient stress signals in said structure;
   said transmitter coil and said receiver coil being wound adjacent said first and second thin ferromagnetic strips, respectively, said guided waves moving perpendicular to said first and second thin ferromagnetic strips.

13. An apparatus for nondestructive, short term inspection or long term monitoring of a structure as recited in claim 12 wherein said residual magnetization is in a lengthwise direction of said thin ferromagnetic strips and said guided wave is a shear wave.

14. An apparatus for nondestructive, short term inspection or long term monitoring of a structure as recited in claim 13 further including a computer for storing a first of said reflected signals and, after appropriate periods of time, comparing new reflected signals with said stored reflected signal to determine if changes have occurred.

15. An apparatus for nondestructive, short term inspection or long term monitoring of a structure as recited in claim 14 wherein a couplant for said coupling of said plurality of said thin ferromagnetic strips is a bonding material, such as epoxy.

16. An apparatus for nondestructive, short term inspection or long term monitoring of a structure as recited in claim 12 wherein a couplant for said coupling of said plurality of said thin ferromagnetic strips is a thick, viscous material, such as honey.

17. An apparatus for nondestructive, short term inspection or long term monitoring of a structure as recited in claim 12 wherein said plurality of thin ferromagnetic strips retain said residual magnetization for a long period of time, such as nickel, grain-oriented silicon steel, or TERFENDOL®.

18. An apparatus for nondestructive, short term inspection or long term monitoring of a structure as recited in claim 15 wherein at least four of said thin ferromagnetic strips are used, two for transmitting and two for receiving, so that direction of travel of said guided wave can be determined, therefore only said reflected signals in a given direction being stored in said computer.

19. An apparatus for nondestructive, short term inspection or long term monitoring of a structure recited in claim 15 wherein said transmitter coil and said receiver coil are coils on a flexible printed circuit board which generates or receives said guided wave in said ferromagnetic strips.

* * * * *